US006942837B2

(12) United States Patent
Frye et al.

(10) Patent No.: US 6,942,837 B2
(45) Date of Patent: Sep. 13, 2005

(54) SYSTEM FOR FILLING A SUBSTRATE WITH A LIQUID SAMPLE

(75) Inventors: Ward Kevin Frye, Foster City, CA (US); Jacob Koppel Freudenthal, Burlingame, CA (US); Terri Christina Labelle, Lathrop, CA (US); Eugene Young, Foster City, CA (US)

(73) Assignee: Applera Corporation, Foster City, CA (US)

( * ) Notice: Subject to any disclaimer, the term of this patent is extended or adjusted under 35 U.S.C. 154(b) by 375 days.

(21) Appl. No.: 09/848,270

(22) Filed: May 4, 2001

(65) Prior Publication Data

US 2001/0029794 A1 Oct. 18, 2001

Related U.S. Application Data

(62) Division of application No. 09/549,382, filed on Apr. 13, 2000, now Pat. No. 6,272,939.
(60) Provisional application No. 60/159,554, filed on Oct. 15, 1999.

(51) Int. Cl.[7] .............................. B01L 3/00; C12M 1/34
(52) U.S. Cl. .................... 422/104; 422/102; 422/82.05; 435/288.7; 435/307.1; 435/288.4
(58) Field of Search .......................... 422/99, 102, 104, 422/61, 82.05; 436/164, 165; 435/287.1, 287.8, 288.7, 307.1, 288.4

(56) References Cited

U.S. PATENT DOCUMENTS

| | | | |
|---|---|---|---|
| 3,080,759 A | 3/1963 | McQuaid | 73/863.73 |
| 3,933,165 A | 1/1976 | Budzak et al. | 73/863.73 |
| 4,892,409 A | 1/1990 | Smith | |

(Continued)

FOREIGN PATENT DOCUMENTS

| | | |
|---|---|---|
| DE | 197 39 119 A1 | 5/1999 |
| DE | 197 48 211 A | 5/1999 |
| EP | 0 895 240 A1 | 2/1999 |

(Continued)

OTHER PUBLICATIONS

Landergren, U., Kaiser, R., Sanders, J. and Hood, L, "A ligase m ediated gene detection technique", 'Science 241:1077–80 (Apr. 1988).
Nickerson, D., Kaiser, R., Lappin, S., Stewart, J., Hood, L. and Landegren U. "Autom ated DNA diagnostics using an ELISA–based oligonucleotide assay", Proc. Natl. Acad. Sci USA 87:8923–27 (Aug. 1990).
Grossman, P., Bloch, W., Brinson, E., Chang C., Eggerding, F., Fung. S., Iovenniscl, D., Woo, S. and Winn–Deen, E. "High–density multiplex detection of nucleic acid sequences: olignucleotide ligation assay and sequencecoded separation ", Nucl. Acids Res. 22:4627–34 (Apr. 1994).

Primary Examiner—Lyle A. Alexander
(74) Attorney, Agent, or Firm—Finnegan, Henderson, Farabow, Garrett & Dunner, L.L.P.

(57) ABSTRACT

A system for filling a substrate having at least one chamber with a liquid sample is provided. The system in one embodiment includes a substrate defining a network of passageways including at least one chamber for the liquid sample, and an adapter. The adapter includes a fill reservoir for the liquid sample, a vacuum port for attachment to a vacuum source, and at least two channels. One channel allows a vacuum to be imparted to the network, and the other channel allows the liquid sample to be introduced into the network. The system also includes a mechanism that sequentially closes and opens at least one of the channels so that a vacuum can first be introduced to the substrate and thereafter the liquid sample introduced to the substrate for permitting the vacuum to urge the liquid sample to flow from the fill reservoir into the substrate. An apparatus for positioning a substrate with a plurality of sample detection chambers in a detection unit is also provided.

3 Claims, 28 Drawing Sheets

U.S. PATENT DOCUMENTS

| | | | |
|---|---|---|---|
| 4,948,564 A | | 8/1990 | Root et al. |
| 5,210,015 A | | 5/1993 | Gelfand et al. |
| 5,415,839 A | * | 5/1995 | Zaun et al. .................... 422/64 |
| 5,444,520 A | | 8/1995 | Murano |
| 5,538,848 A | | 7/1996 | Livak et al. |
| 5,780,717 A | | 7/1998 | Wise et al. .............. 73/864.81 |
| 5,837,197 A | * | 11/1998 | Porrazzo et al. .............. 422/61 |
| 5,928,907 A | | 7/1999 | Woudenberg et al. |
| 6,015,674 A | | 1/2000 | Woudenberg et al. |
| 6,159,368 A | | 12/2000 | Moring et al. |
| 6,272,939 B1 | | 8/2001 | Frye et al. |
| 6,563,581 B1 | * | 5/2003 | Oldham et al. ............. 356/317 |

FOREIGN PATENT DOCUMENTS

| | | |
|---|---|---|
| EP | 0 955 097 A1 | 11/1999 |
| EP | 1 088 590 A1 | 4/2001 |
| GB | 2 207 245 A | 1/1989 |
| WO | 91/17239 | 11/1991 |
| WO | 97/36681 | 10/1997 |
| WO | WO 98/15356 A | 4/1998 |
| WO | WO 01/28684 A2 | 4/2001 |

* cited by examiner

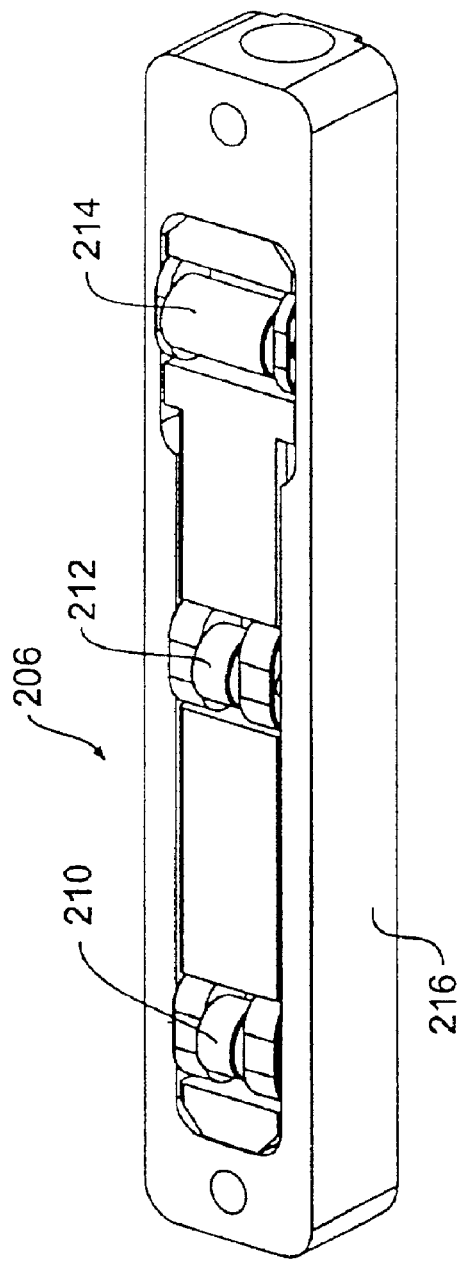
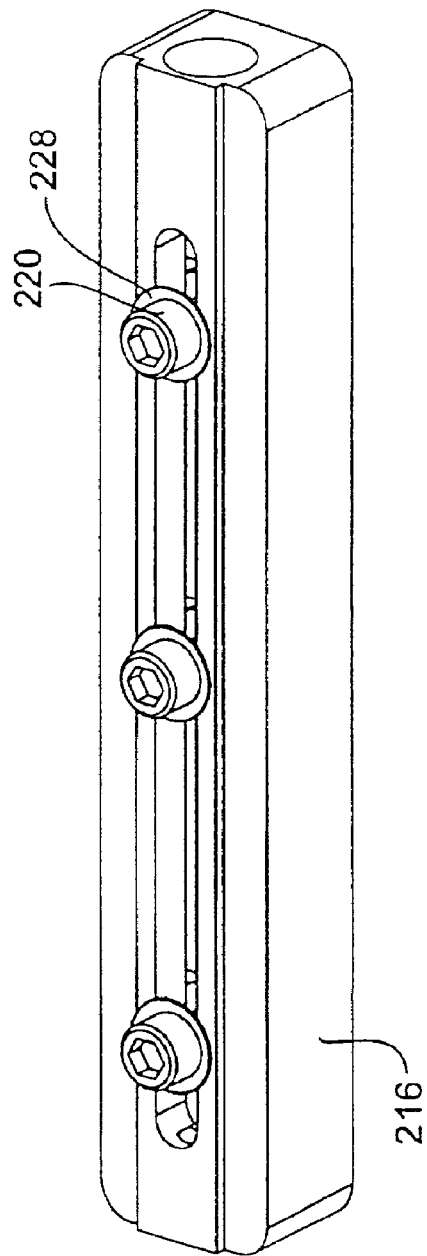
FIG. 21
FIG. 22

SYSTEM FOR FILLING A SUBSTRATE WITH A LIQUID SAMPLE

This is a division of application Ser. No. 09/549,382, filed Apr. 13, 2000 now U.S. Pat. No. 6,272,939, and claims the benefit of U.S. provisional application no. 60/159,554, filed Oct. 15, 1999 which is incorporated herein by reference.

BACKGROUND OF THE INVENTION

1. Field of the Invention

The present invention relates in one aspect to liquid loading of vessels. In a particular embodiment, this invention relates to a system for filling a substrate having at least one chamber with a liquid sample, such as a system for filling a card-like member having a plurality of sample detection chambers with a liquid sample to react with reagents located in the sample detection chambers during thermal cycling of a polymerase chain reaction (PCR) process. In another aspect, the present invention relates to an apparatus for positioning a substrate in a detection unit.

2. Description of the Related Art

Biological testing has become an important tool in detecting and monitoring diseases. Recent developments in the field have spurred growth in the number of tests that are performed. Performing great numbers of these tests may be costly and time consuming. One way of minimizing costs is to reduce the size of the samples that are being tested and increase the number of samples that can be tested during each run of a thermal cycling unit or other like device. Therefore, it is often desirable to test a large number of samples having a small sample size. A substrate for simultaneously testing a large number of analytes which has a small sample size and a large number of detection chambers has been described in WO97/36681, assigned to the assignee of the present application, the contents of which are hereby incorporated by reference herein.

It is desirable to provide a system for filling a substrate having a large number of small detection chambers in a manner that is safe, reliable, and fast. Previous methods require laborious steps and can expose the operator performing these steps to reagents. Moreover, previous methods may permit undue contamination between detection chambers and may be prone to the presence of air bubbles in the detection chambers. In light of the foregoing, there is a need for a system and method that overcomes the disadvantages of the previous methods.

SUMMARY OF THE INVENTION

The advantages and purposes of the invention will be set forth in part in the description which follows, and in part will be apparent from the description, or may be appreciated by practice of the invention. The advantages and purposes of the invention will be realized and attained by means of the elements and combinations particularly pointed out in the appended claims.

In one aspect, the invention includes a system for filling a substrate having at least one chamber with a liquid sample. The system in one embodiment includes a substrate defining a network of passageways including at least one chamber for the liquid sample, and an adapter. The adapter includes a fill reservoir for the liquid sample, a vacuum port for attachment to a vacuum source, and at least two channels. One channel allows a vacuum to be imparted to the network, and the other channel allows the liquid sample to be introduced into the network. The system also includes a mechanism that sequentially closes and opens at least one of the channels so that a vacuum can first be introduced to the substrate and thereafter the liquid sample introduced to the substrate for permitting the vacuum to urge the liquid sample to flow from the fill reservoir into the substrate. The mechanism for sequentially closing and opening includes a frame that holds at least one adapter and substrate, and also includes a valving mechanism that sequentially sealingly engages and disengages the channels of the adapter.

In another aspect, the invention includes a substrate filling member configured for connection to a substrate having at least one chamber for a liquid sample. The substrate filling member in one embodiment includes a base, a reservoir on the base configured to receive a liquid sample, a vacuum port on the base configured for attachment to a vacuum source, and a plurality of fluid channels in the base. The plurality of fluid channels includes a first fluid channel for permitting a vacuum to be imparted to the substrate and at least one fluid channel of the filling member at a first setting. The plurality of fluid channels permits the liquid sample from the fill reservoir to flow into the at least one chamber of the substrate at a second setting.

In a further aspect of the invention, the invention includes a filling station for controlling the filling of substrate having at least one chamber with a liquid sample. In one embodiment, the filling station includes a base portion receiving the substrate and an adapter. The adapter includes a filling reservoir, vacuum port, and a plurality of flow paths. The filling station also includes an actuator selectively directing the liquid sample into the at least one sample chamber of the substrate when the actuator is in a predetermined position. The actuator includes a plurality of valving structures for selectively opening and closing flow paths on the adapter according to a predetermined procedure.

In a further aspect of the invention, the invention includes a method of filling at least one chamber of a substrate with a liquid sample. The method includes the step of providing a substrate having at least one chamber for containing a liquid sample and at least one path for accessing the chamber. The method further includes the step of providing an adapter for connection to the substrate, the adapter having a fill reservoir for the liquid sample, a vacuum port, and a plurality of channels. Next, a control apparatus is closed so that the substrate and adapter are fixed therein, and a liquid sample is inserted into the fill reservoir of the adapter. A vacuum is then introduced to the chamber and path of the substrate. The control apparatus is actuated in order to expose the liquid sample in the fill reservoir to the vacuum so that the liquid sample is urged towards the chamber of the substrate.

In another aspect of the invention, the invention includes an apparatus for positioning a substrate with a plurality of sample detection chambers in a detection unit. The apparatus includes a frame assembly and lens assembly. The frame assembly is configured so that a substrate may be positioned in the frame assembly. The lens assembly includes a plurality of plates. One of the plates includes a lens plate in which at least one lens is located for focusing a light which passes through the lens.

In a further aspect, the invention is a method of positioning a substrate with at least one sample detection chamber into a sample detection instrument. The method includes the steps of opening the sample detection instrument, placing a support frame on the sample detection instrument, and inserting a substrate with at least one sample detection chamber in the support frame. The method also includes placing a lens plate over the substrate and support frame, and aligning at least one hole in the lens plate relative to the sample detection chamber of the substrate. The sample detection instrument is then closed.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

FIG. 21 shows a bottom perspective view of the wheel assembly of FIG. 18;

FIG. 22 shows a top perspective view of an assembled wheel assembly of FIG. 18;

DESCRIPTION OF THE PREFERRED EMBODIMENTS

Figure 1:
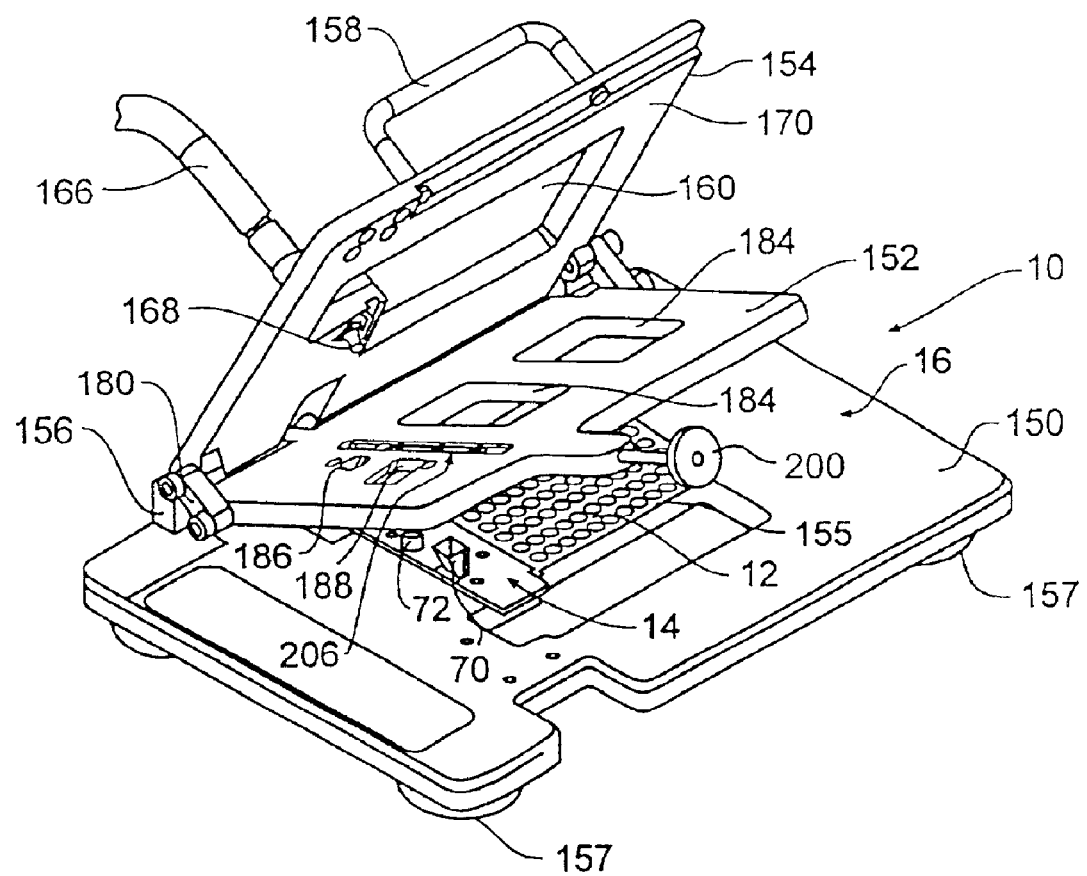
FIG. 1 shows a perspective view of a system for filling a substrate with a liquid sample according to the invention, with a filling station in an open position.
Figure 2:
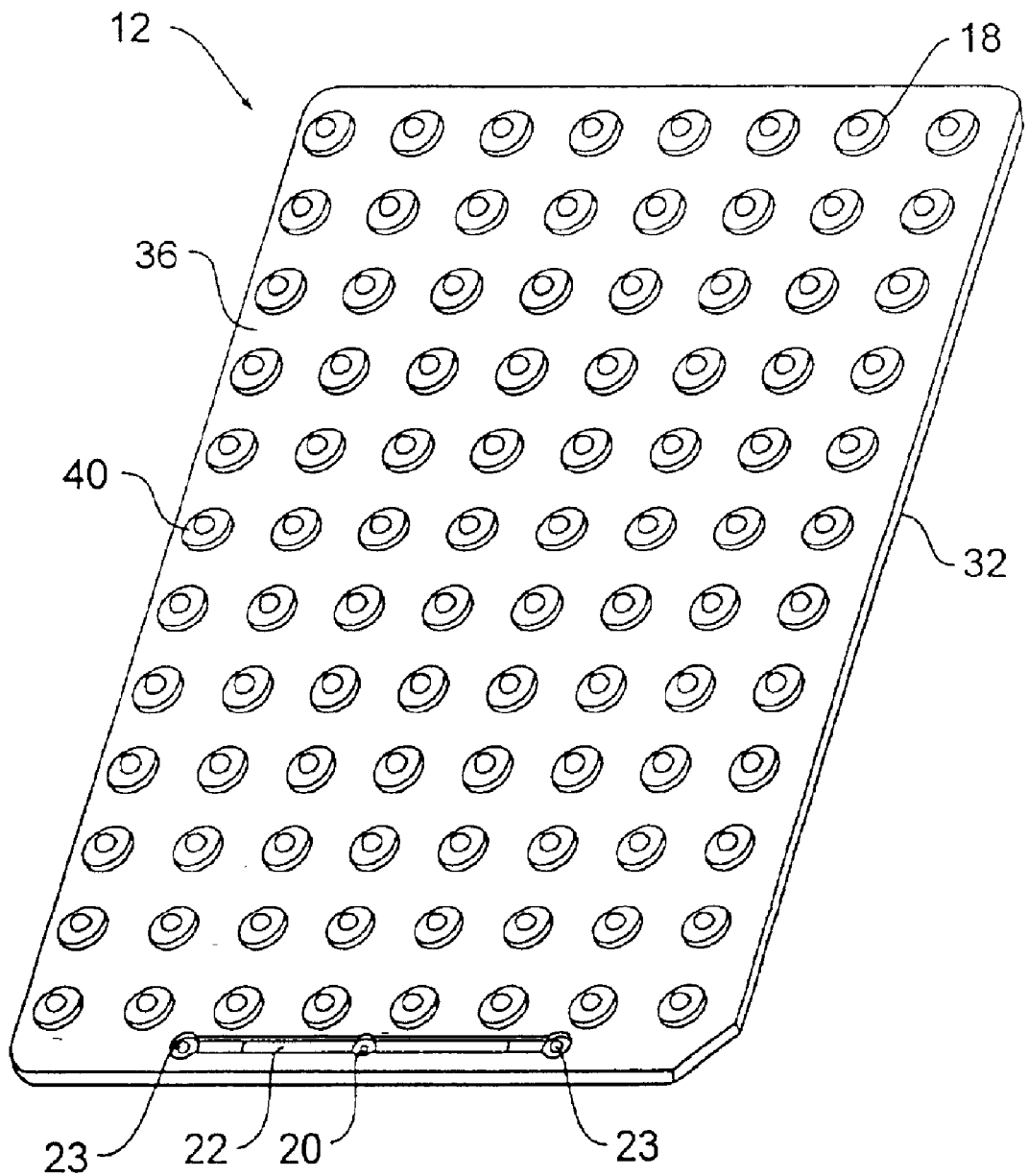
FIG. 2 shows a perspective view of a microcard of the system of FIG. 1.
Figure 3:
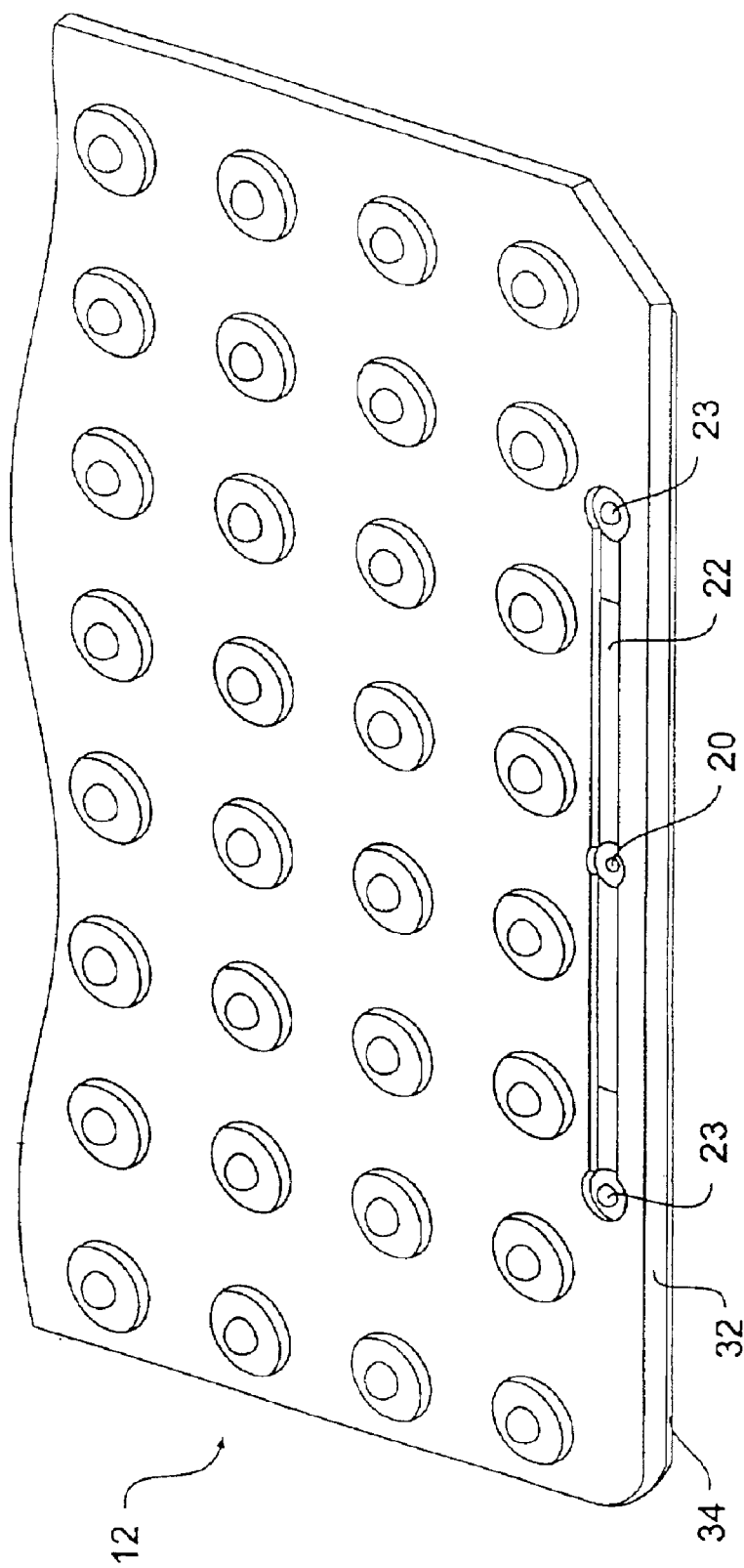
FIG. 3 shows a close-up perspective view of the microcard of FIG. 2.

Reference will now be made in detail to the present preferred embodiments of the invention, examples of which are illustrated in the accompanying drawings. Wherever possible, the same reference numbers will be used throughout the drawings to refer to the same or like parts.

In accordance with the present invention, a system for filling a substrate, such as a microcard, having at least one chamber with a liquid sample is provided. Each chamber preferably contains an analyte-specific reagent that reacts with a selected analyte that may be present in the liquid sample. In one embodiment of the present invention, the system includes a substrate defining a network of passageways including at least one chamber for the liquid sample, and in a typical microcard, ninety-six chambers connected by a network of passageways are provided. As embodied herein and shown in FIGS. 1–25, the system 10 for filling a substrate with a liquid sample includes a substrate 12; an adapter 14; and a filling station 16.

The system 10 includes a substrate with a network 17 of passageways, as best shown in FIGS. 2–5. The substrate 12 is shown as being generally rectangular in the general shape of a credit card, therefore, the substrate is often referred to as a microcard. The substrate can be a variety of other shapes and sizes compared to the embodiment shown in the Figures. By way of example only, in one embodiment, the substrate is approximately 7 cm×11 cm×0.2 cm. The substrate 12 defines a network 17 of passageways including a plurality of sample detection chambers 18. Each sample detection chamber can hold a predefined volume of liquid sample. In one embodiment of the present invention, each sample detection chamber has a volume of approximately 1 $\mu$l. This volume can be varied depending on the specific application. By utilizing reduced volume sample chambers, the amount of reagent and analyte that are consumed decreases, resulting in cost savings. In addition, more samples can be tested on a given substrate, thereby reducing the total number of tests that need to be run. While the drawings illustrate an exemplary embodiment showing ninety-six sample detection chambers 18, the number and arrangement of chambers can be varied. For example, a substrate with three hundred and eighty-four sample detection chambers, as well as other numbers of chambers, is also consistent with the present invention.

As embodied herein and shown for example in FIGS. 2–5, the substrate 12 is provided with a sample inlet port 20 for the entrance of the liquid sample into the network 17 of passageways. The sample inlet port 20 is appropriately located, such as preferably in the center, of a shaped attachment feature, such as attachment/bladder groove 22, in one plate such as top plate 32 of the substrate 12, and extends through the attachment/bladder groove 22. Attachment/bladder groove 22 extends across a portion of the width of the top surface of the substrate plate 32 in a region outside of the sample detection chambers 18. The attachment/bladder groove 22 is defined by a top surface and side surfaces. The top surface of the attachment/bladder groove 22 is slightly recessed from the top surface of the top plate 32 adjacent the attachment/bladder groove.

The attachment/bladder groove 22 serves several functions. First, attachment pins 23 are provided at each end of the attachment/bladder groove. During attachment of the adapter 14 to the substrate 12, these cylindrical attachment pins 23 are positioned inside attachment projections 132 of the adapter to assist in aligning the adapter 14 onto the substrate 12. The connection between the adapter and substrate is made more secure by the provision of attachment pins 23 and attachment projections 132. Second, the attachment/bladder groove 22 provides an air pocket for the liquid sample in the network of passageways. After the substrate is filled with the liquid sample and sealed, as will be discussed below, the liquid sample in the network 17 of passageways may undergo temperature fluctuations, especially if the substrate is used for thermal cycling operations. The liquid sample in the network 17 of passageways expands as the temperature of the sample increases. The attachment/bladder groove 22 provides a pocket of air above the network 17 of passageways so that the sample may expand without significantly increasing the pressure on the substrate. This is useful to protect against leakage in the substrate due potential rupture of the seals. The liquid sample may flow into the attachment/bladder groove 22 through sample port 20. In one embodiment, the air pocket of the attachment/bladder groove 22 is located above and distal from the network 17 of passageways so that the air in the attachment/bladder groove 22 is substantially prevented from mixing with the liquid sample.

Figure 4:
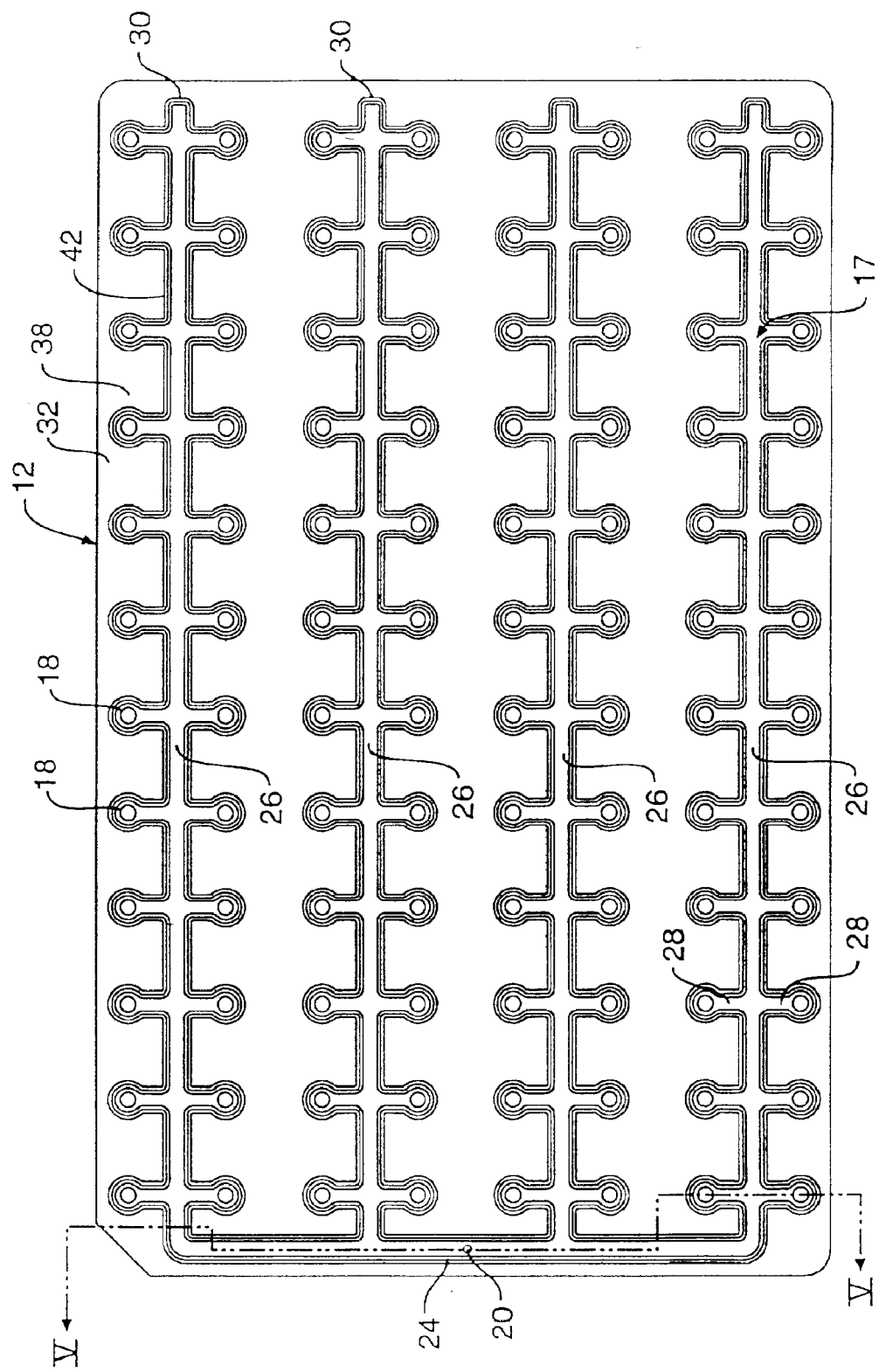
FIG. 4 shows a bottom view of the microcard of FIG. 2.

As best shown in FIG. 4, the network 17 of passageways of the substrate includes at least a sample inlet delivery passageway 24 on an edge of the bottom surface of the top plate 32; four longitudinal delivery passageways 26 that extend from the sample inlet delivery passageway 24, as best shown in FIG. 4; dead-end passageways 28; and sample detection chambers 18. In one embodiment of the present invention, the longitudinal delivery passageways 26 extend in a perpendicular direction from the sample inlet delivery passageway 24. The sample inlet delivery passageway 24 extends parallel to the attachment/bladder groove 22, but on an edge of the bottom surface 38 of the top plate 32. The parallel longitudinal delivery passageways 26 are positioned along the substrate 12 as indicated. A plurality of pairs of dead-end fluid passageways or connections 28 branch off of each longitudinal delivery passageway 26. Dead-end fluid passageways 28 connect the sample detection chambers 18 to the longitudinal delivery passageways 26. Each pair of sample detection chambers 18 is located on opposite sides of the longitudinal delivery passageway 26. In one embodiment, each longitudinal delivery passageway 26 has twenty-four sample detection chambers extending therefrom arranged as twelve pairs. Therefore, the substrate of the one embodiment contains ninety-six sample detection chambers. This number, as well as the pattern of arrangement and network connections making up a suitable microcard, can clearly be varied.

As shown in FIG. 4, the end of each longitudinal delivery passageway 26 is a dead end 30. The specific arrangement of the longitudinal delivery passageways, dead end fluid connections, and sample detection chambers shown in the figures is by way of example only. The passageways, connections, and chambers may be arranged in any suitable manner. By way of example only, all of the chambers could be placed on one side of the longitudinal delivery passageways. Alternately, the number of passageways and grooves, and their relative positions, can be greatly varied. The filling system of the present invention could be utilized with any of a large variety of different substrate designs and is not limited to the specific design shown in the figures.

Figure 5:
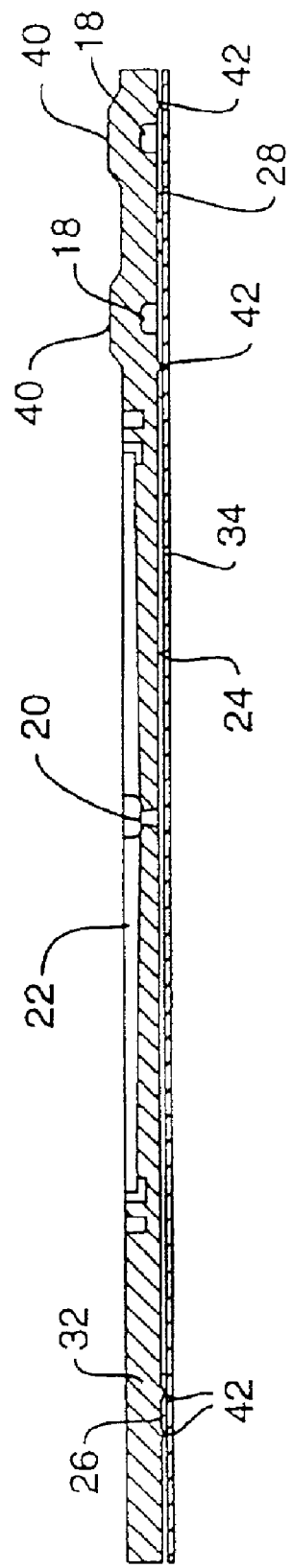
FIG. 5 shows a sectional view of the microcard along line V—V of FIG. 4.
Figure 6:
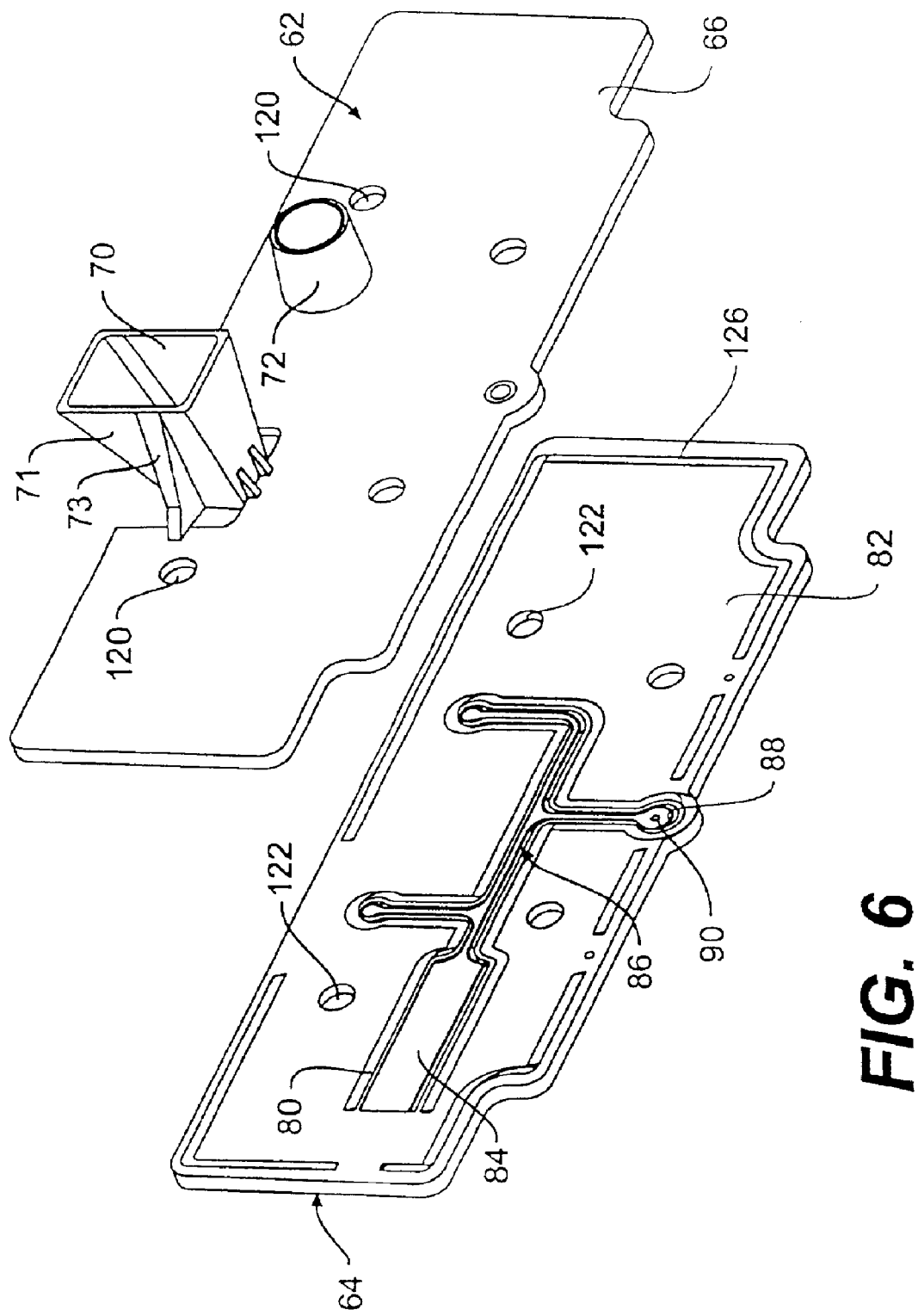
FIG. 6 shows a perspective view of an adapter assembly of the system of FIG. 1.

As embodied herein and shown in FIGS. 2–5, substrate 12 is preferably composed of a top plate 32 and a bottom plate 34. The top plate 32 has an upper surface 36 that contains raised surfaces 40, as best shown in FIGS. 2–5. The raised surfaces 40 define the top portion of each sample detection chamber 18. The top plate 32 contains v-shaped ridges 42 (also called energy directors) which are slightly raised from the lower surface 38 of the top plate. Because the bottom plate 34 is flat with a substantially smooth top surface, the top and bottom plate 32 and 34 touch only along the ridges 42 when they are brought together, as best shown in FIG. 5. The ridges 42 therefore define the network 17 of passages for the substrate. For example, in FIG. 5, the ridges 42, bottom surface of the top plate 32, and top surface of the bottom plate 34 define the longitudinal delivery passageway 26. The cross-section of FIG. 5 also shows the dead-end fluid passageway 28 and sample detection chambers 18 being defined by the ridges 42, bottom surface of the top plate 32 and the top surface of the bottom plate 34. FIG. 5 also shows the sample delivery passageway 24 between the bottom surface of the top plate 32 and the top surface of the bottom plate 34.

Although the figures show the network of passageways being defined by ridges protruding from the top plate, the network of passageways could be defined in any number of other manners. For example, in one alternate embodiment, ridges could protrude from the bottom plate, with the top plate being substantially smooth. In another alternate embodiment, either or both of the top and bottom plate could be provided with indentations that define the network of passageways. In this embodiment, no ridges would be necessary. Other suitable methods for defining a network of passageways that can maintain a sufficient vacuum and be filled with a liquid sample, may be acceptable in the present invention.

The top and bottom plate 32 and 34 can be joined to each other by a variety of methods. The top and bottom plate should be sealingly joined so that the network of passageways may come under a vacuum when a vacuum source is applied to the substrate. Moreover, the plates 32 and 34 should be joined so that the liquid sample does not leak from the substrate. The method of joinder should also be able to withstand temperature fluctuations that can occur during thermal cycling. In the preferred embodiment, the top and bottom plates are bonded together using ultrasonic welding. During a typical ultrasonic welding procedure, a large weight is placed on the two plates and forced to vibrate. The vibrations cause the plastic to melt at the portions of the plates that are touching each other, that is, along the portion of ridges 42 that are in contact with the smooth top surface of the bottom plate 34. The ultrasonic welding technique is completed when the ridges (energy directors) are partially melted to the smooth top surface of the bottom plate 34. For example, in one application of the present invention, the plates are ultrasonically welded until a certain percentage of the ridges are melted, such as 80%. However, the desired amount of melting of the ridges can be significantly less than this value and still provide an adequate seal. At this point in the procedure, the ridges 42 have formed the network of passageways and sealed the passageways of the system while leaving open the sample inlet hole 20. Although the embodiment described above connects the plates 32 and 34 using ultrasonic welding, other suitable methods such as the use of adhesives, pressure-sealing, or heat curing may also be used. In yet another approach, the bonding is accomplished using an adhesive gasket layer which is placed between the two substrate plates.

The top and bottom plates 32 and 34 may be made out of any suitable material that can be manufactured according to the required specifications, can withstand any temperature fluctuations that may later occur, i.e., during thermal cycling or other operations performed on the substrate, and can be suitably joined. In addition, if the substrate is to later be used for optical detection, the top of each sample detection chamber 18 must be optically transparent for detection of the reaction. For this purpose, silica-based glasses, quartz, polycarbonate, or any optically transparent plastic layer, for example, may be used. If the substrate is going to be used in PCR reactions, the material should be PCR compatible, and the material should be preferably be substantially flourescence free. In one embodiment, the material for the top plate is a polycarbonate manufactured by "BAYER"™, referred to as FCR 2458-1112 and the material for the bottom plate is a 0.015 inch thickness polycarbonate manufactured by "BAYER"™, referred to as Makrofol DE1-1 D. The substrate plates can be formed by a variety of methods known in the art. For example, top plate 32 may be injection molded, whereas bottom plate 34 may be die-cut. Any other suitable method of manufacturing the plates is also acceptable.

Prior to assembly of the top and bottom plates 32 and 34, an analyte-specific reagent is typically placed in each detection chamber 18. One or more of the detection chambers may be left empty to function as a control. These analyte-specific reagents in the detection chambers may be adapted to detect a wide variety of analyte classes in the liquid sample, including polynucleotides, polypeptides, polysaccharides, and small molecule analytes, by way of example only. The polynucleotide analytes are detected by any suitable method, such as polymerase chain reaction, ligase chain reaction, oligonucleotide ligation assay, or hybridization assay. A preferred method of polynucleotide detection is the exonuclease assay referred to as "TAQMAN"™. Non-polynucleotide analytes may also be detected by any suitable method, such as antibody/antigen binding. The above detection methods are well-known in the art. They are described in detail in the following articles and patents: U.S. Pat. No. 5,210,015 of Gelfand et al.; U.S. Pat. No. 5,538,848 of Livak et al.; WO 91/17239 of Barany et al. published on Nov. 14, 1991; "A Ligase-Mediated Gene Detection Technique" by Landegren et al published in Science 241:1077–90 (1988); "High-density multiplex detection of nucleic acid sequences: oligonucleotide ligation assay and sequence-coded separation" by Grossman et al., published in Nucleic Acid Research 22:4527–34 (1994); and "Automated DNA diagnostics using an ELISA-based oligonucleotide ligation assay" by Nickerson et al., published in Proc. Natl. Acad. Sci. USA 87:8923–27 (1990).

Further in accordance with the present invention, the system also includes an adapter to assist in the filling of the substrate with a liquid sample at the filling station. As embodied herein and shown in FIGS. 6–12, adapter 14 preferably comprises two plates, such as a top plate 62 and bottom plate 64. The top plate 62 includes a fill reservoir 70 for receiving the fluid sample from a pipette or other dispensing device, and a vacuum port 72 for allowing a vacuum to be imparted in the network 17 of passageways of the substrate 12. The fill reservoir 70 and vacuum port 72 are located on the top surface 66 of the top plate 62 as shown in the FIGS. 6–8.

In one embodiment shown in the figures, the fill reservoir 70 is a square funnel with a square opening at the top and tapering side walls 71 extending to the top surface 66 of the top plate 62. Structural supports 73 in the shape of buttresses support the tapered side walls. The fill reservoir can be of any variety of convenient shapes besides that shown in the figure, such as cylindrical, conical, or rectangular. The fill reservoir can be filled by a variety of automatic or manual processes. In a typical embodiment, the liquid sample is introduced into the fill reservoir by a hand held pipette. The fill reservoir 70 should have a sufficient volume so that the entire network 17 of passageways, including the sample detection chambers 18, can be filled upon operation of the filling station 16 as described below. According to one embodiment of the present invention with a ninety-six chamber substrate, the fill reservoir is typically designed to hold at least 300 μl of liquid sample. The size of the fill reservoir is a function of the size of the sample detection chambers 18 and the passageways 24, 26 and 28, and can therefore be varied. The liquid sample flows out of the fill reservoir 70 through an opening 74 which passes through the top plate 62 to the bottom surface 68. The liquid sample flows into fill channels located between the top plate 62 and bottom plate 64 as will be described below. The fill reservoir of the present embodiment is shown by way of example only. The fill reservoir does not need to be integral with the top plate, but could instead be a separate member that is attached to the adapter.

Figure 7:
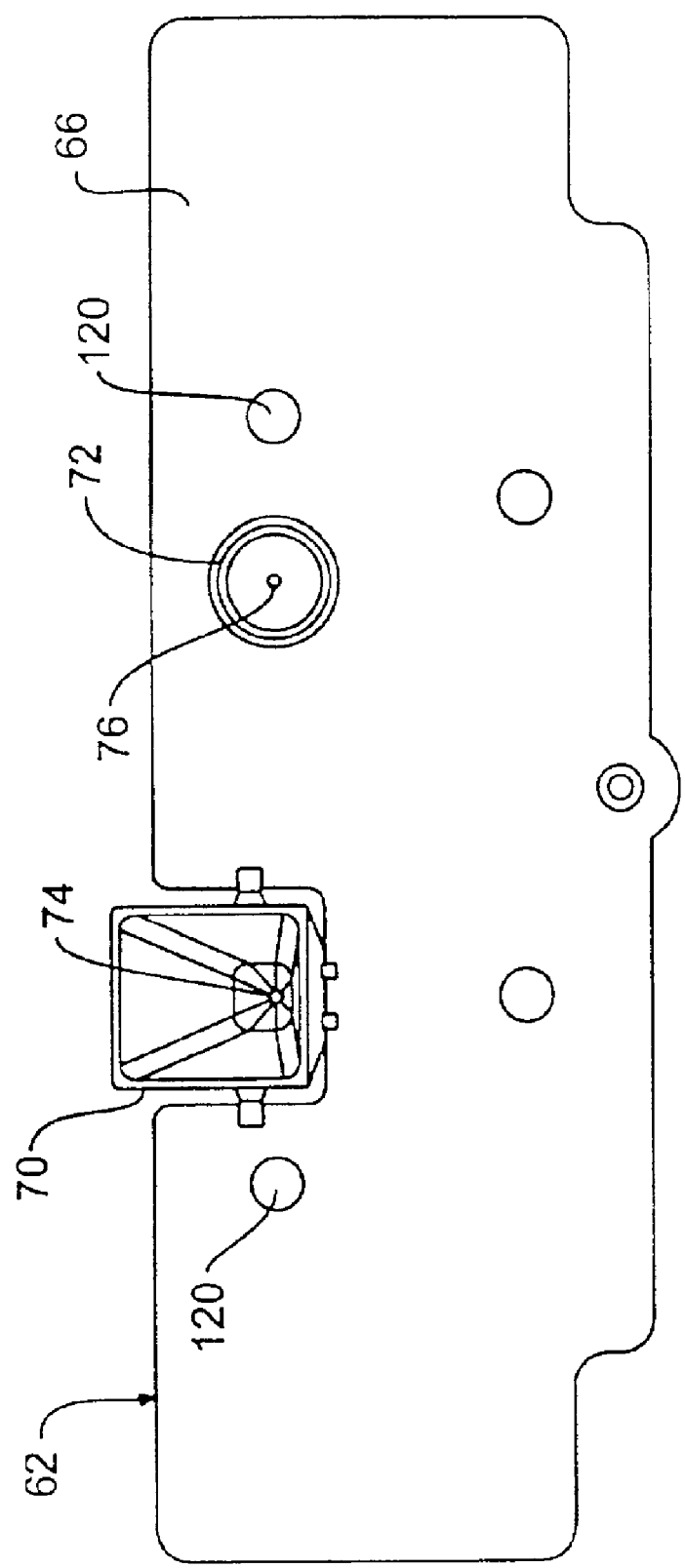
FIG. 7 shows a top view of a top plate of the adapter assembly of FIG. 6.
Figure 8:
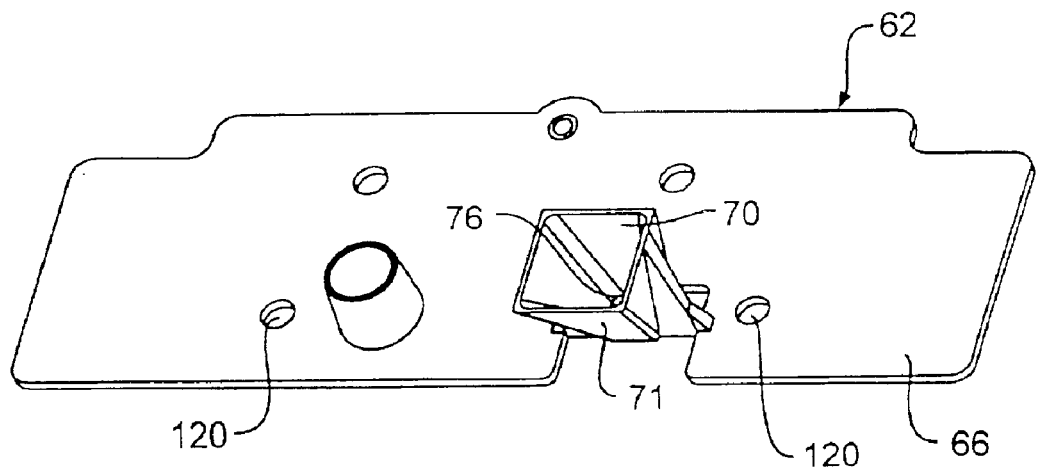
FIG. 8 shows a perspective view of the top surface of the top plate of FIG. 7.
Figure 9:
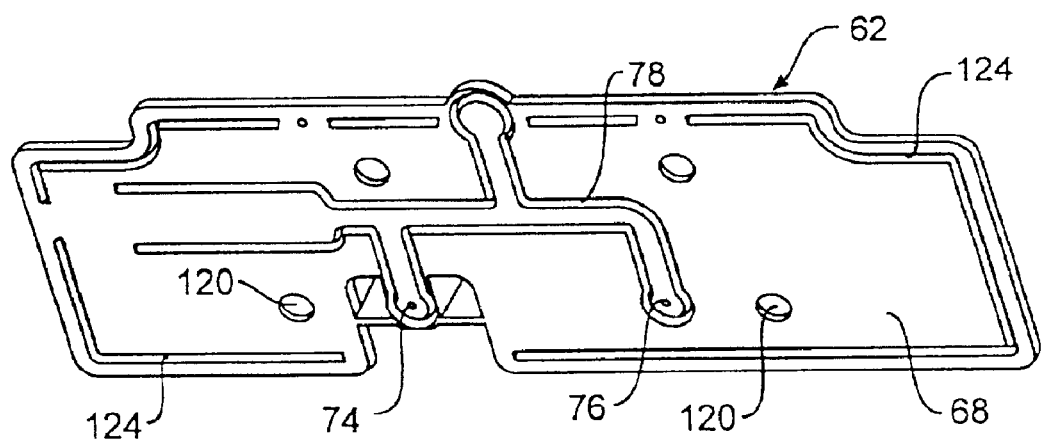
FIG. 9 shows a perspective view of the bottom surface of the top plate of FIG. 8.

The vacuum port 72 is shown in the shape of a cylindrical projection extending from the top surface 66 of the top plate 62. The vacuum port 72 may have any shape that is suitable for a vacuum connection on the filling station (to be described below). A vacuum port hole 76 is provided in the center of the vacuum port 72, as best shown in FIGS. 7–9. Vacuum port hole 76 passes through the top plate 62 to the bottom surface 68. In an alternate design, the vacuum port could be provided on the bottom plate subject to the design of the filling station. As will be discussed in greater detail, the provision of the vacuum port allows a vacuum to be applied to a network of passageways of the substrate. The vacuum range is typically applied by a vacuum pump. In the present invention, the vacuum range for ideal performance is approximately 0 to 500 microns. In a typical operation of one embodiment of the present invention, a vacuum in the range of 50 to 150 microns is desired.

The top plate 62 of the adapter further includes recesses or grooves 78 on the bottom surface 68 thereof for mating with ridges 80 of a top surface 82 of the bottom plate 64 as described below. The top surface 82 of the bottom plate 64 of the adapter has a channel surface 84 between the respective ridges. The channel surface 84 is slightly lowered from the main top surface 82 of the bottom plate 64. When the top plate 62 and bottom plate 64 are attached, the ridges 80 of the bottom plate 64 mate with the recesses or grooves 78 of the top plate 62 to form fluid channels 86.

Figure 10:
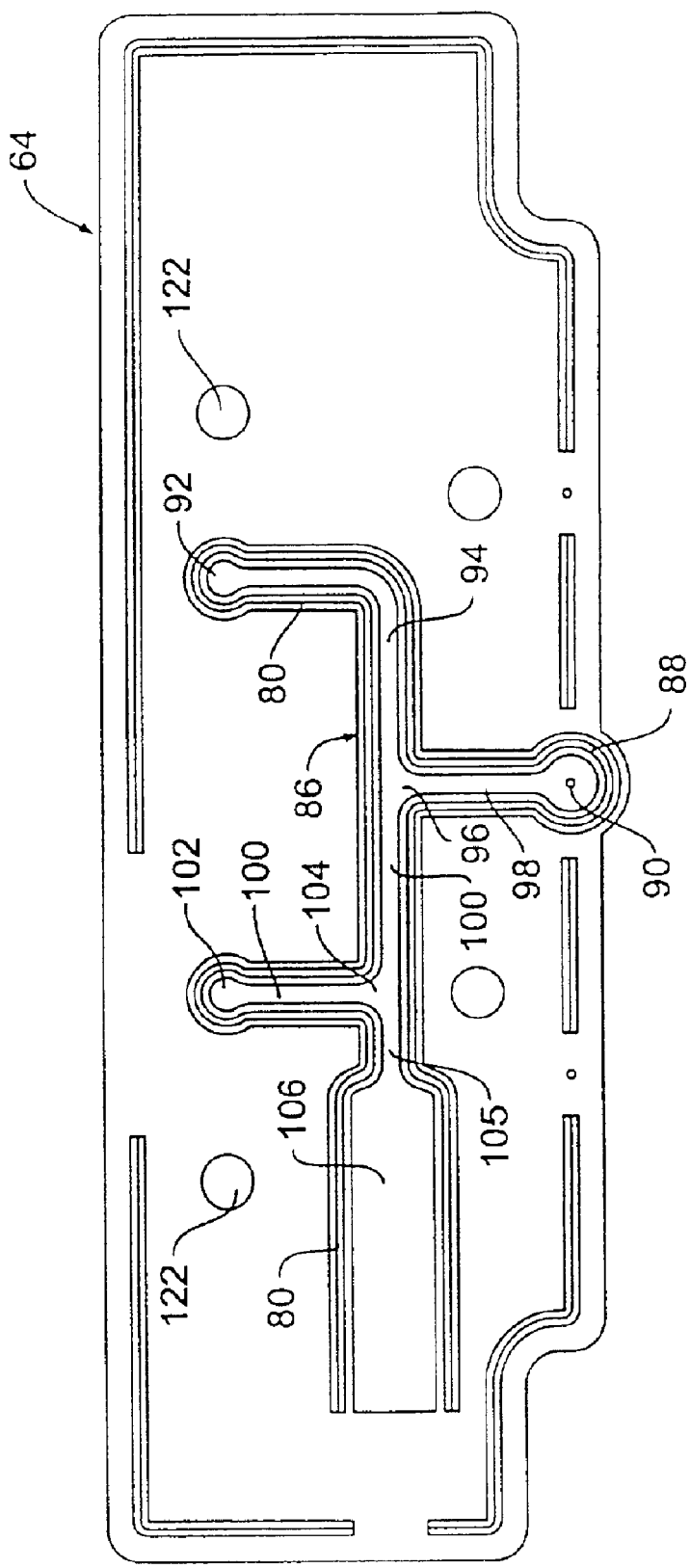
FIG. 10 shows a top view of a bottom plate of the adapter assembly of FIG. 6.
Figure 11:
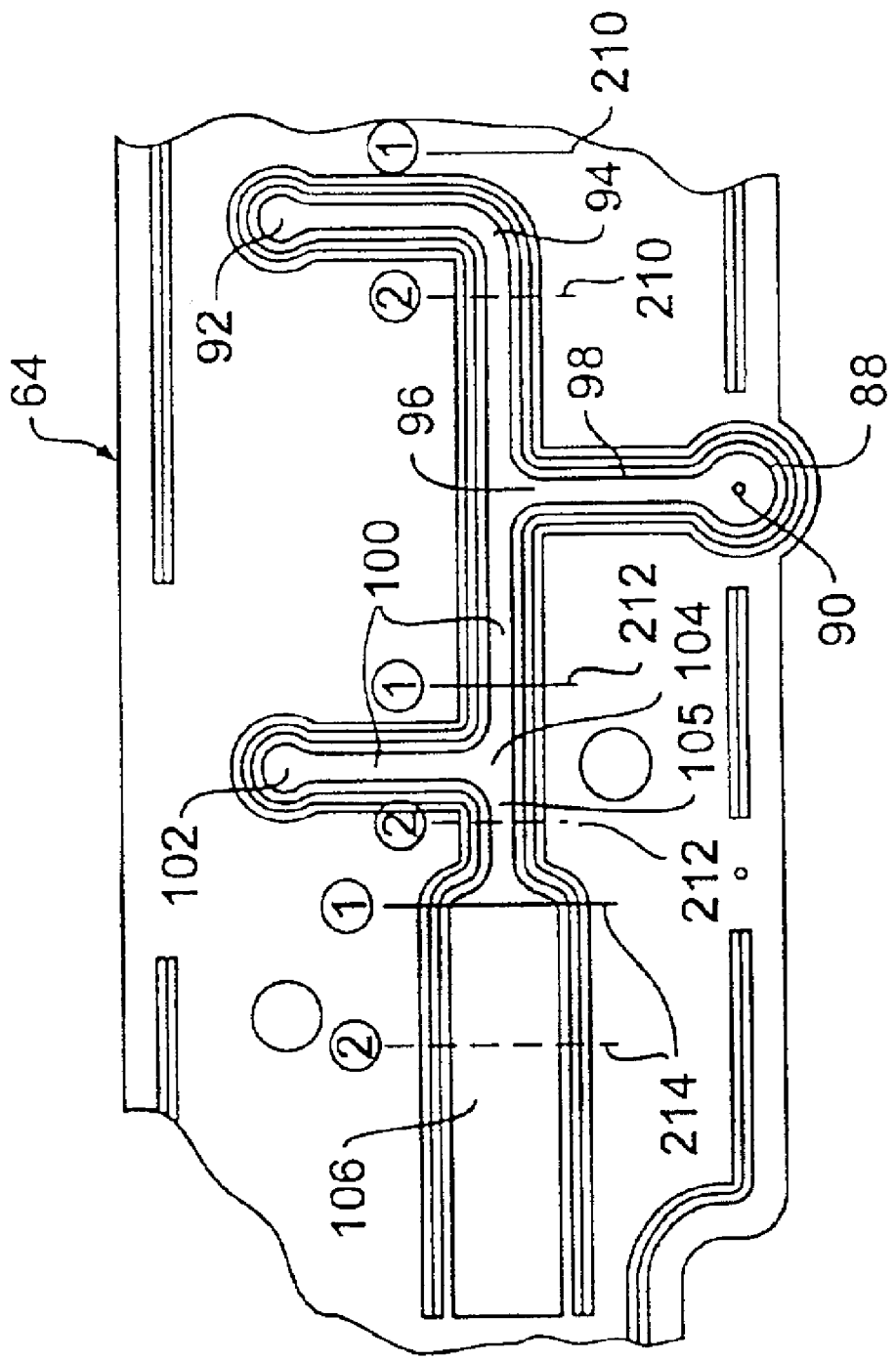
FIG. 11 shows a top view of the bottom plate of FIG. 10, but showing the relative locations of a wheel assembly in a first and second position.

The mating ridges 80 and grooves 78 define a plurality of fluid channels 86 for the vacuum, liquid sample, and ambient air. As shown in FIGS. 10–11, a vacuum channel 94 extends from the entrance 92 to the vacuum channel immediately below the vacuum port hole 76 to the juncture 96 with a perpendicularly extending exit port channel 98. The exit port channel 98 leads to an exit port 88 with a small circular opening 90 in the center thereof. A fill channel 100 extends from the entrance 102 to the fill channel immediately below the fill reservoir 70 to the juncture 96 with the exit port channel 98. The portion of the fill channel 102 that bends perpendicular is referred to as juncture 104. A bladder connection channel 105 is located between the fill channel juncture 104 and the bladder channel 106. The bladder connection channel 105 has the same width as the vacuum and fill channels 94 and 100. A main bladder channel 106 extends from the fill channel juncture 104 to the ambient air. The main bladder channel 106 has a larger width than the other channels in order to perform a priming function which will be discussed later. These channels formed by the top and bottom plates serve to allow air to flow out of the substrate and liquid sample to flow into the substrate.

The top and bottom plates 62 and 64 of the adapter 14 are preferably made out of an elastomeric material so that the channels can be opened and closed by pressing on the channels with a valving mechanism. One material that is suitable for use with the present invention is "DUPONT"™ ELVAX 150, although many other materials are also suitable for the present invention. The top and bottom plates 62 and 64 may be attached to each other by a variety of methods. In a preferred method, ultraviolet (UV) activated adhesive is used to bond the two plates together. After flipping the top plate 62 over, the recesses 78 in the top plate 62 are filled with a continuous bead UV activated adhesive, and the bottom plate 64 is laid on the top plate 62 so that the ridges 80 fit into the recesses 78 of the top plate. The plates are then placed under a UV light to cure the adhesive, and the top and bottom plate are thereby bonded together. It is important that the plates are adequately sealed together so that a vacuum can be formed in the vacuum channel and so that no liquid sample may leak.

In another embodiment, the top and bottom plates of the adapter may be modified so that the top plate contains the ridges 80 and the bottom plate has the recesses 78. In this alternate configuration, the adhesive may be poured into the recesses 78 in the top surface of the bottom plate 64, and then the top plate 62 can be fit on top of the bottom plate so that the ridges mate with the recesses.

In a further embodiment, the fluid channels 86 are not formed by any ridges or recesses in the top and bottom plates, but by one or more thin adhesive plates with channels formed therein. These thin adhesive plates could be placed between a substantially smooth bottom surface of the top plate and a substantially smooth top surface of the bottom plate. By providing for this middle layer of adhesive, the injection mold for the top and bottom plates could be simplified. Moreover, a separate step of inserting adhesive in recesses would no longer be required. In another embodiment, heat sealing could be utilized to heat and seal localized areas to define the fluid channels 86. With this method, adhesives would not be required.

In another embodiment, flexible tubing might be utilized to form the fluid "channels." The tubing could be placed on a plate so that engagement structures may move relative to the tubes. The tubes could have a greater diameter at the bladder channel portion so that the priming function (described later) could be performed. Clearly, the embodiments discussed above are exemplary only, other variations may also be used in order to define the fluid channels 86 in the adapter.

The top and bottom plates 62 and 64 of the adapter include respective alignment holes 120 and 122. The two alignment holes 120 of the top plate 62 are arranged to mate with the two alignment holes 122 of the bottom plate. During insertion of the adapter 14 and substrate 12 into the filling station 16, two alignment pins 159 projecting from the base of the filling station pass through the alignment holes 120 and 122 to ensure the proper alignment of the adapter in the filling station. Other methods of aligning the adapter in the fill station may also be contemplated, such as having pins on the adapter to mate with holes in the fill station.

The top plate 62 of the adapter further includes circumferential recesses or grooves 124 located around the circumference of the bottom surface 68 of the top plate, as best shown in FIG. 9. The circumferential grooves 124 mate with circumferential ridges 126 located around the circumference of the top surface 82 of the bottom plate. During the attachment method of the top and bottom plates previously described, the circumferential recesses 124 are filled with the same adhesive as the other recesses 78 to provide additional bonding between the top and bottom plates.

Figure 12:
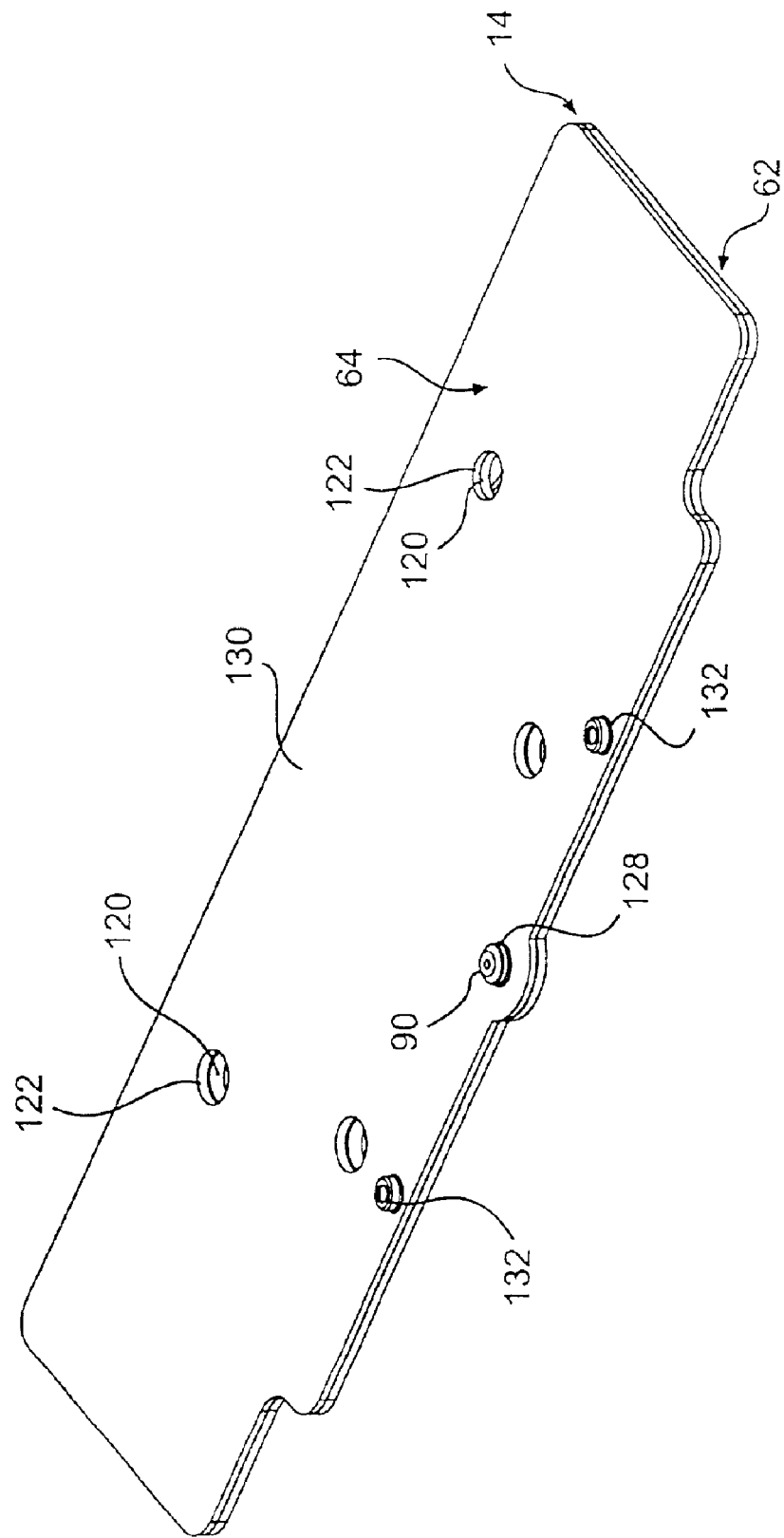
FIG. 12 shows a bottom perspective view of the adapter assembly of FIG. 6.

The liquid sample may flow out of the adapter 14 through the small circular opening 90 in the exit port 88. The exit port 88 includes a cylindrical projection 128 that projects from the bottom surface 130 of the bottom plate 64, as best shown in FIG. 12 which shows the substrate in an upside-down position. The cylindrical projection 128 includes the small circular opening 90 through which the liquid sample exits. The cylindrical projection 128 is designed to mate with the sample inlet hole 20 so that a fluid-tight connection occurs between the adapter 14 and the substrate 12. The bottom surface 130 of the bottom plate 64 also includes attachment projections 132. The attachment projections 132 are hollow cylinders with openings in the inside for mating with the attachment pins 23 of the substrate. The openings in the cylinder are sized to fit closely with the attachment pins 23 of the substrate. The cylindrical projection 128 and attachment projections 132 extend into the attachment/bladder groove 22 of the substrate during assembly.

Figure 13:
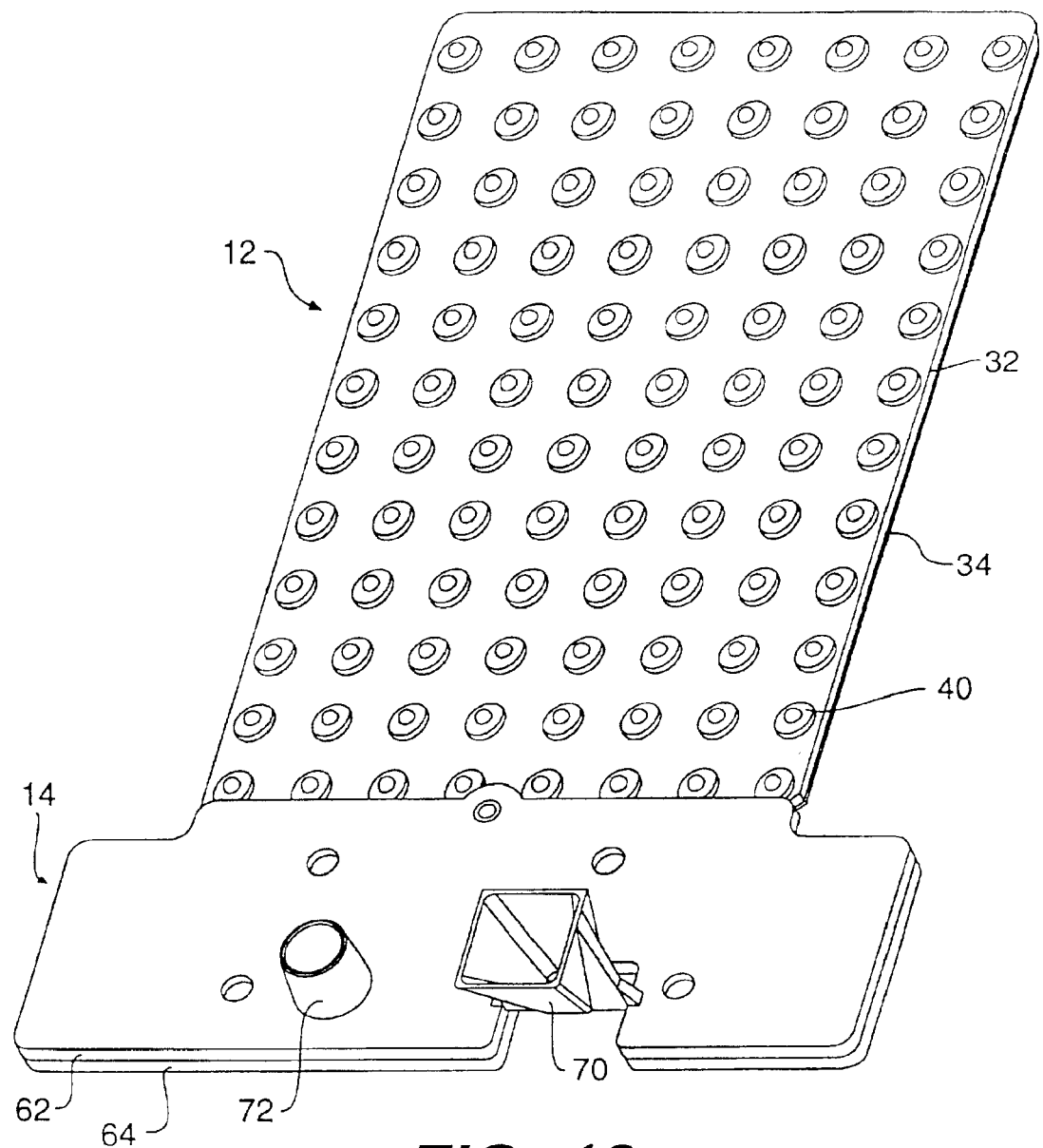
FIG. 13 shows a perspective view of the adapter assembly connected to the microcard.

The adapter is attached to the substrate by placing the adapter on the edge of the top surface of the substrate as shown in FIG. 13, thereby inserting the attachment pins 23 into the attachment projections 132. During the attachment of the adapter to the substrate, the cylindrical projection 28 of the adapter aligns with the sample inlet hole 20. The end of the cylindrical projection 28 abuts against the top surface of the attachment/bladder groove 22 to form a seal therewith. A small strip of adhesive (not shown) may also be provided for the area of overlap between the adapter 14 and substrate 12. This adhesive strip helps to ensure that the adapter is firmly connected to the substrate to form a seal. The material that is used for the adhesive strip depends on the operations that will be performed on the substrate. If the liquid sample is to be used for PCR operations, it is desirable to have an adhesive that is PCR compatible, in addition to being able to securely adhere to the material of the adapter and substrate. A double-coated polyester adhesive strip such as "3M" Part 1513 with a 0.0034" thickness is suitable with the present invention in one embodiment. A hole is provided in the strip of adhesive so that the cylindrical projection 128 can mate with the sample inlet port 20 without any adhesive interfering with the hole of sample inlet port 20 or the hole 90 of exit port 88. Once the adapter and substrate are adequately connected to one another, they are placed in a filling station.

In accordance with the present invention, the system further includes a valve or mechanism for sequentially closing and opening at least one of the channels of the adapter. As embodied herein and shown in FIGS. 1, and 14–24, a filling station 16 is provided for controlling the filling of the substrate. In the embodiment shown in the figures, the filling station includes a base plate 150, a middle plate 152, and a cover plate 154.

Figure 17:
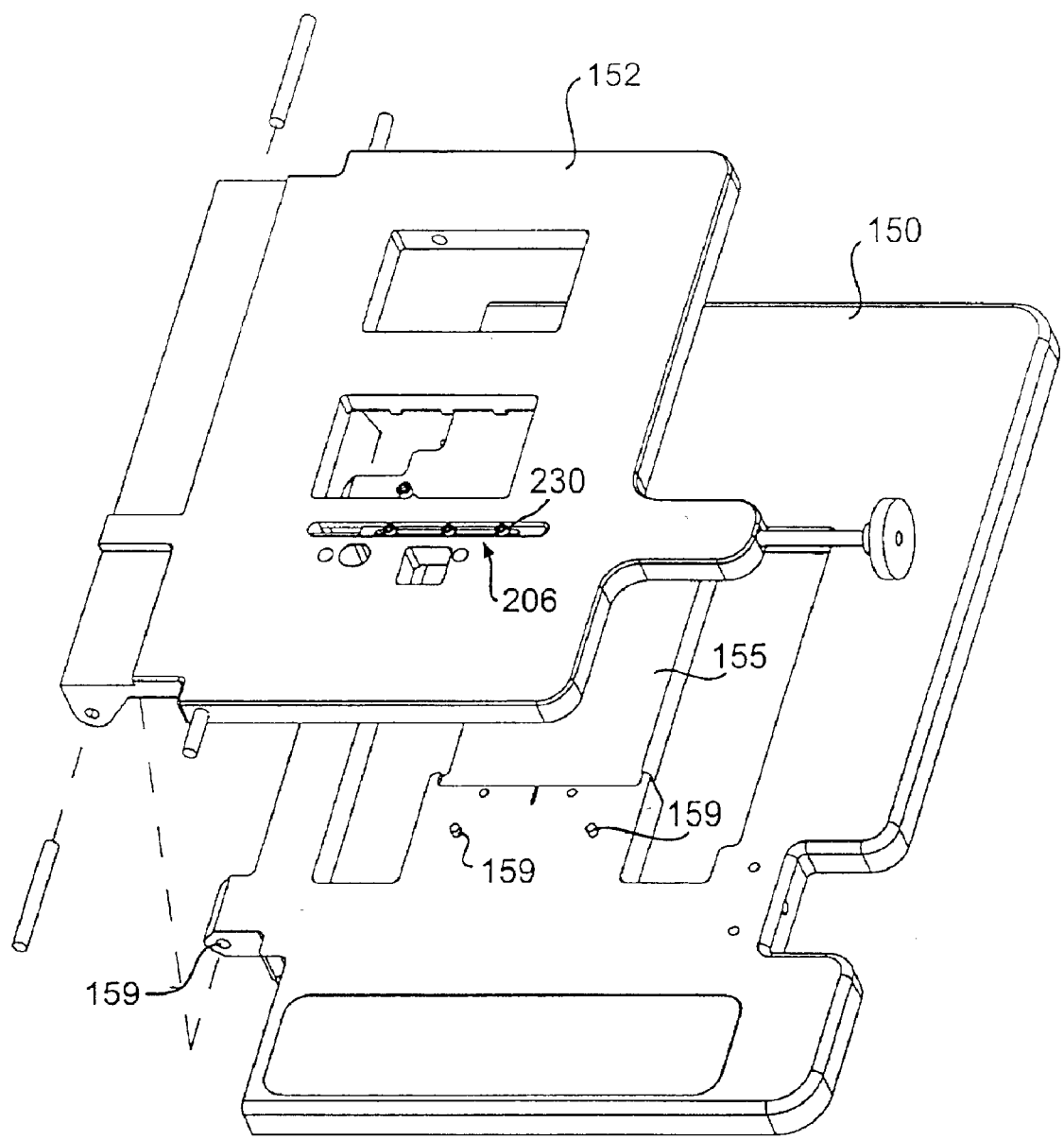
FIG. 17 shows a perspective view of an unassembled middle plate and base plate of the filling station of FIG. 1.
Figure 18:
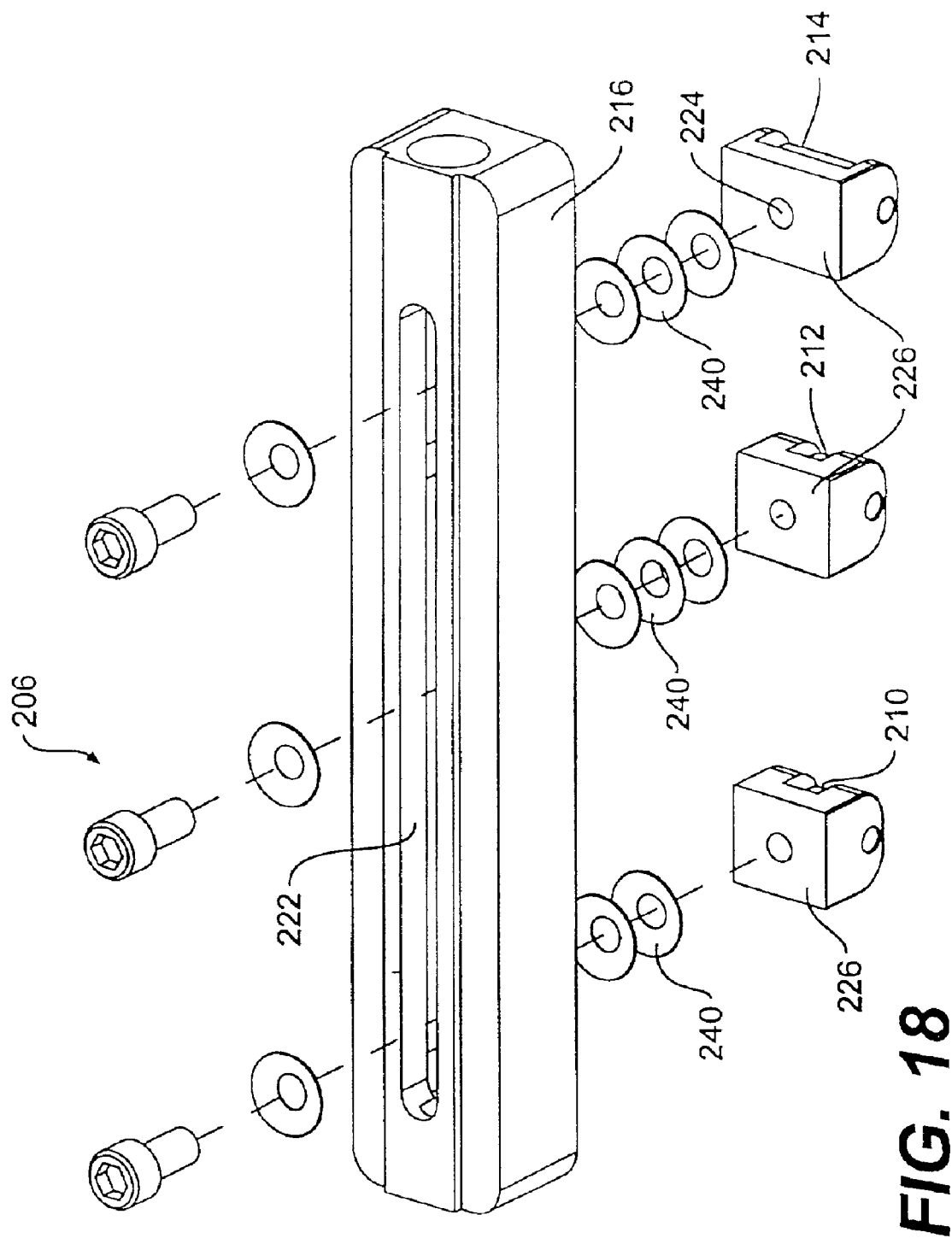
FIG. 18 shows a perspective view of an unassembled wheel assembly of the filling station of FIG. 1.
Figure 19:
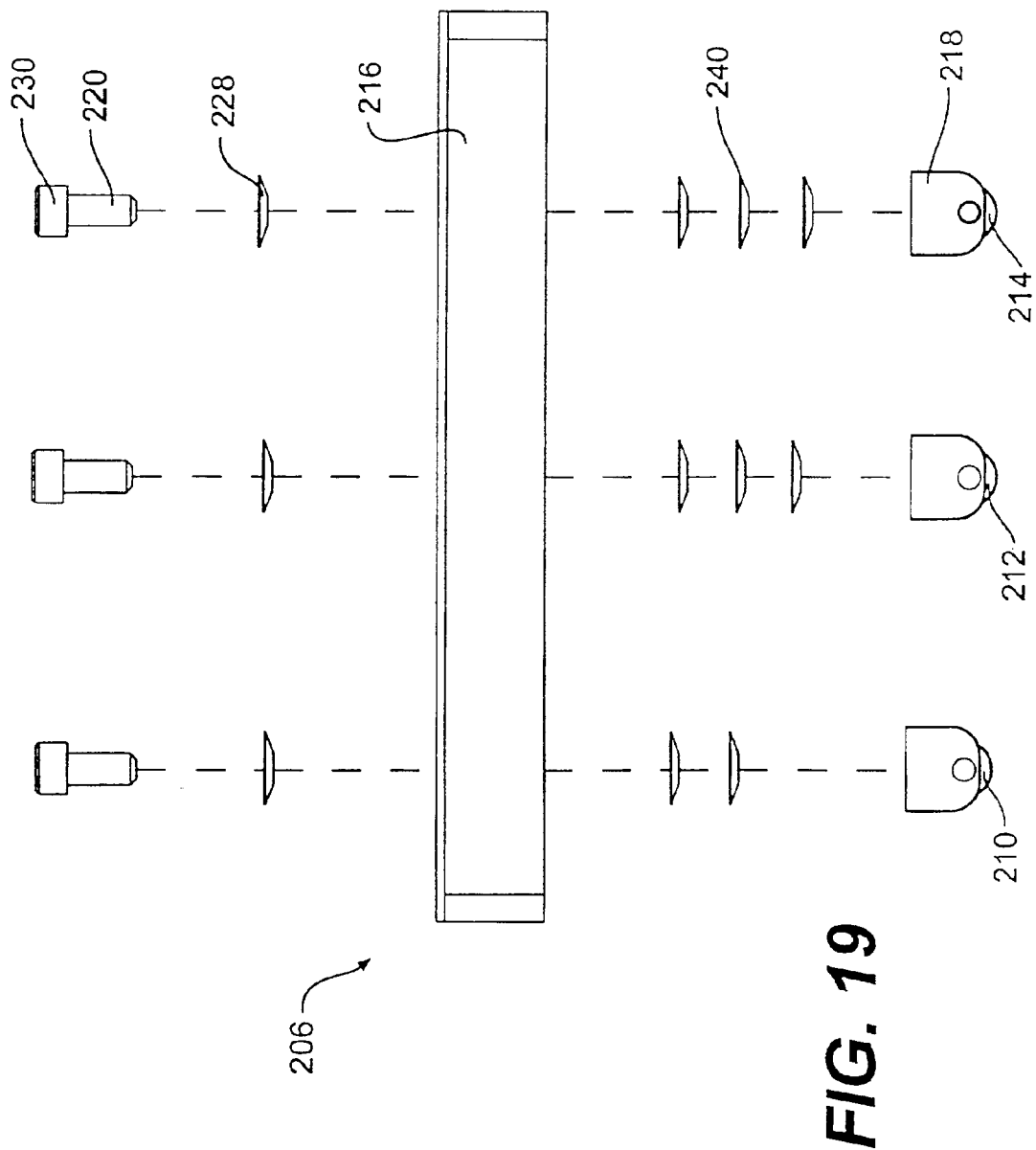
FIG. 19 shows a side view of the unassembled wheel assembly of FIG. 18.
Figure 20:
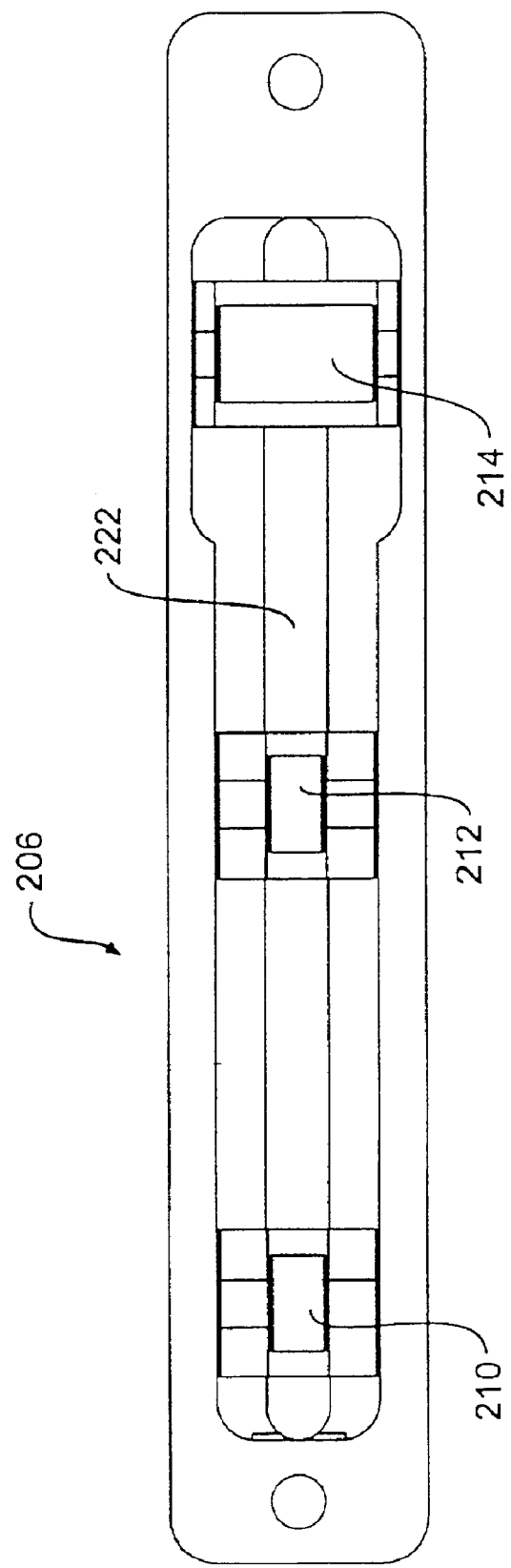
FIG. 20 shows a bottom view of the wheel assembly of FIG. 18.
Figure 23:
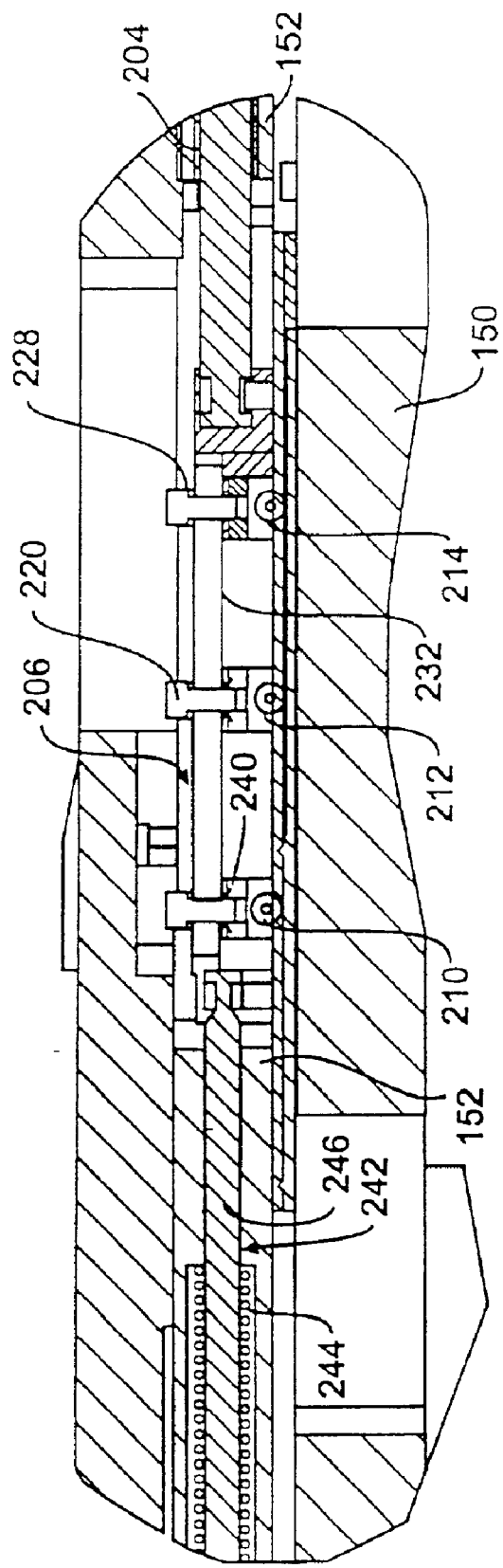
FIG. 23 shows a side sectional view of an actuator of the system of FIG. 1 in a first position.
Figure 24:
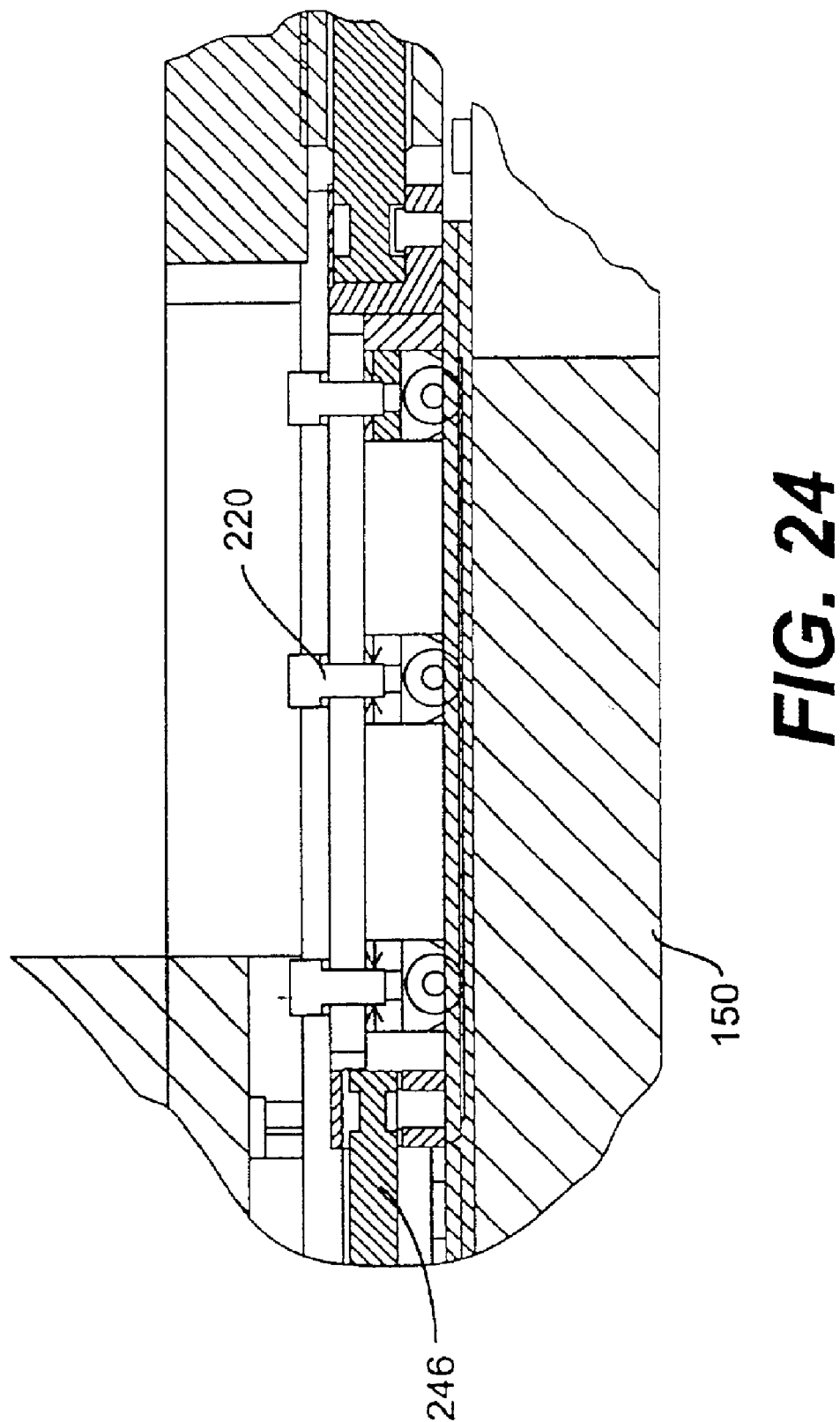
FIG. 24 shows a side sectional view of the actuator of FIG. 22 in a second position.
Figure 25:
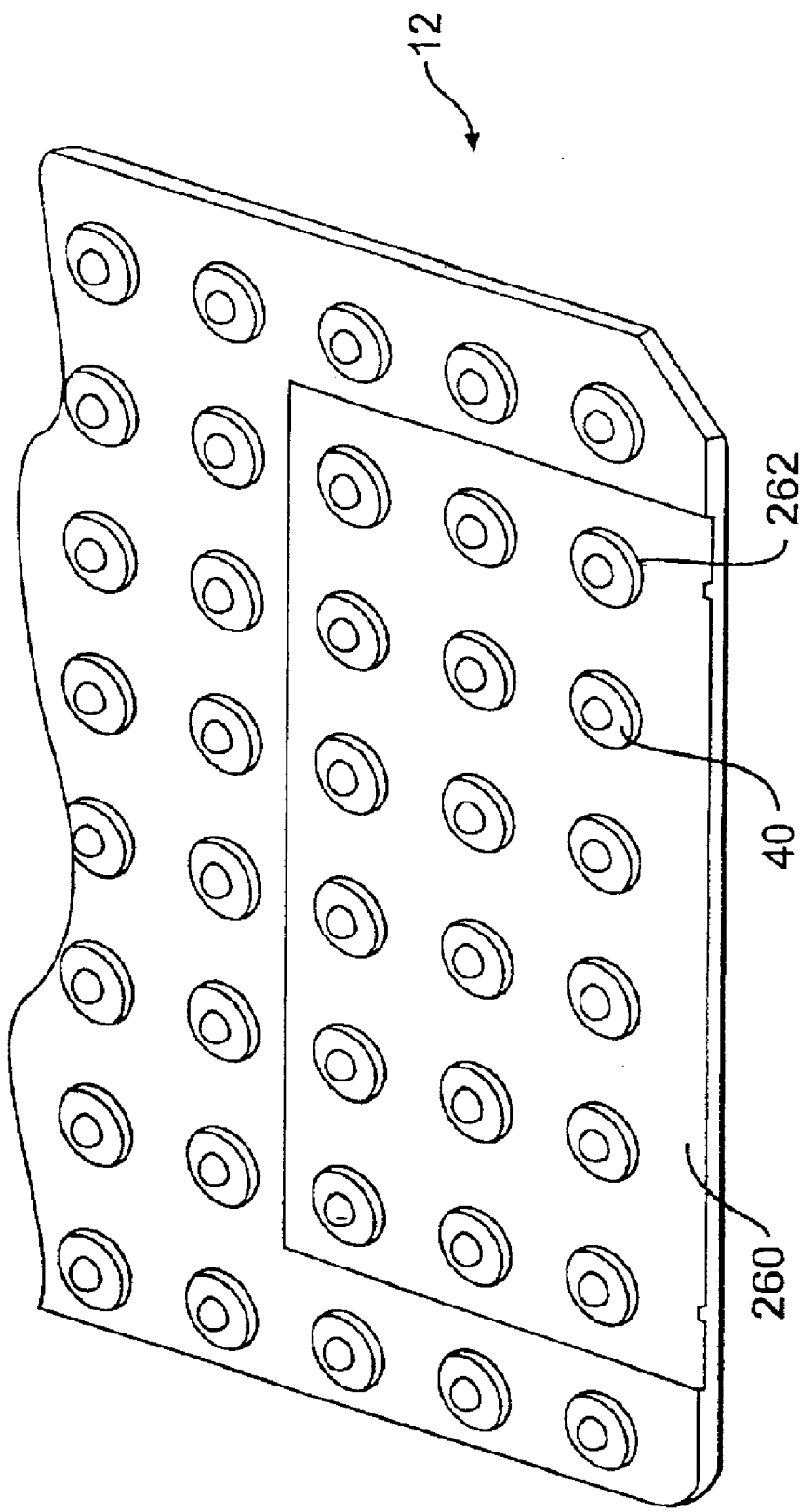
FIG. 25 shows a perspective view of the microcard of FIG. 2 with an adhesive sealing tape.

The base plate 150 includes a recess 155 in which the substrate 12 (with the adapter attached to a portion thereof) is placed. Recess 155 is preferably shaped so that the substrate can be firmly positioned therein. As best shown in FIG. 17, two alignment pins 159 are typically positioned adjacent the recess 155 for projecting through the alignment holes 120, 122 in the top and bottom plates 62, 64 of the adapter. The base plate includes feet 157 on the bottom surface supporting the filling station on a surface such as a table.

The filling station 16 further includes a cover plate 154. As embodied herein and shown in the FIGS. 1, and 14–15, the cover plate 154 is pivoted about the base plate at hinges 156 on the base plate. Cover plate 154 includes a handle 158 so that the cover plate can be opened and closed by an operator. The cover plate 154 further includes a through hole 160 so that the fill reservoir 70 of the adapter can be accessed and so that the actuator (to be described) and portions of the substrate can be visually inspected. A vacuum nozzle 162 is attached to the top surface 164 of the cover plate. A vacuum hose 166 is attached to the vacuum nozzle 162. The end of the vacuum hose typically includes a quick-release valve (not shown) that clicks when the hose is locked into place over the vacuum nozzle. The vacuum nozzle includes a vacuum nipple 168 projecting from the bottom surface 170 of the cover plate 154. The nipple 168 fits snugly into a vacuum hole 172 in the middle plate 152, which will be described below.

The filling station 16 further includes middle plate 152. Middle plate 152 pivots about the base plate at hinge 159 of the base plate, as best shown in FIG. 17. The hinge 159 for the middle plate is preferably located slightly below the hinge 156 for the cover plate. The middle plate 152 is connected to the cover plate 154 by an overcenter linkage 180. The overcenter linkage 180 ensures that the cover plate 154 and middle plate 152 will be pressed strongly against the adapter and substrate when the cover plate is closed by the operator. As the operator closes the cover plate by pivoting about hinge 156, the cover plate will reach an angle at which the resistance to further pivoting greatly increases. Upon overcoming this point, referred to as the "center" point, the overcenter linkage will assist the operator in closing the cover plate and help to firmly press the middle plate against the adapter. The overcenter linkage 180 will also help to ensure that the filling station is not inadvertently opened, because of the force necessary to overcome the bias force of the overcenter linkage.

Figure 14:
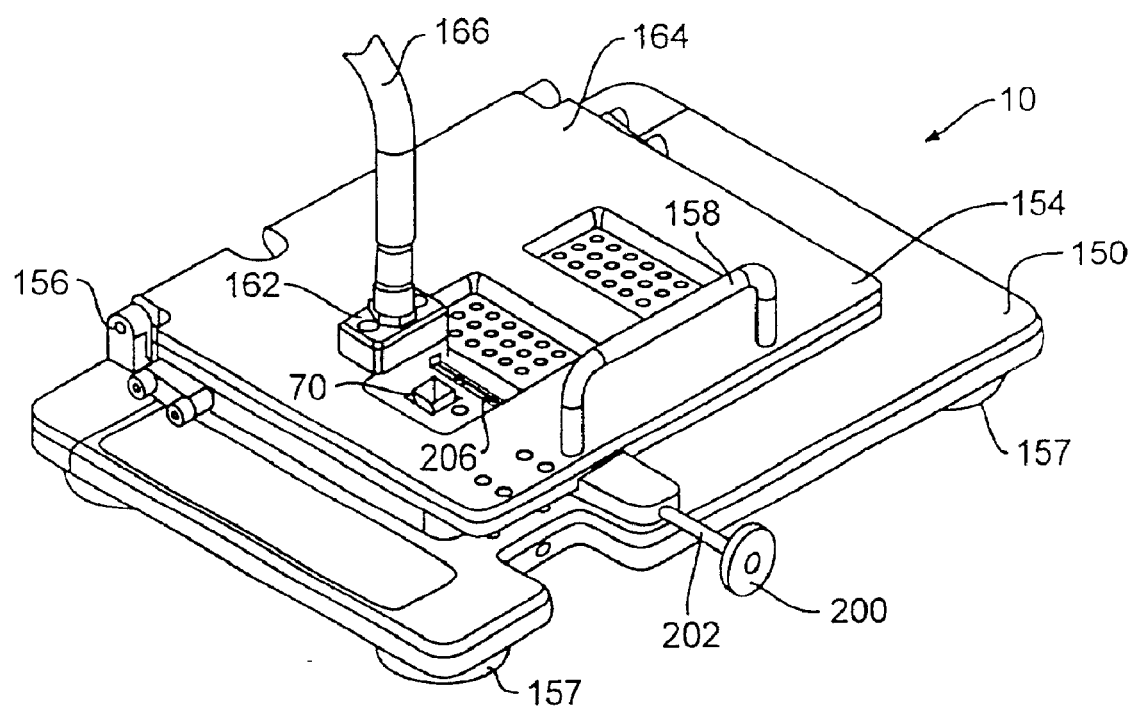
FIG. 14 shows a perspective view of the system of FIG. 1, with the filling station in a closed position.
Figure 15:
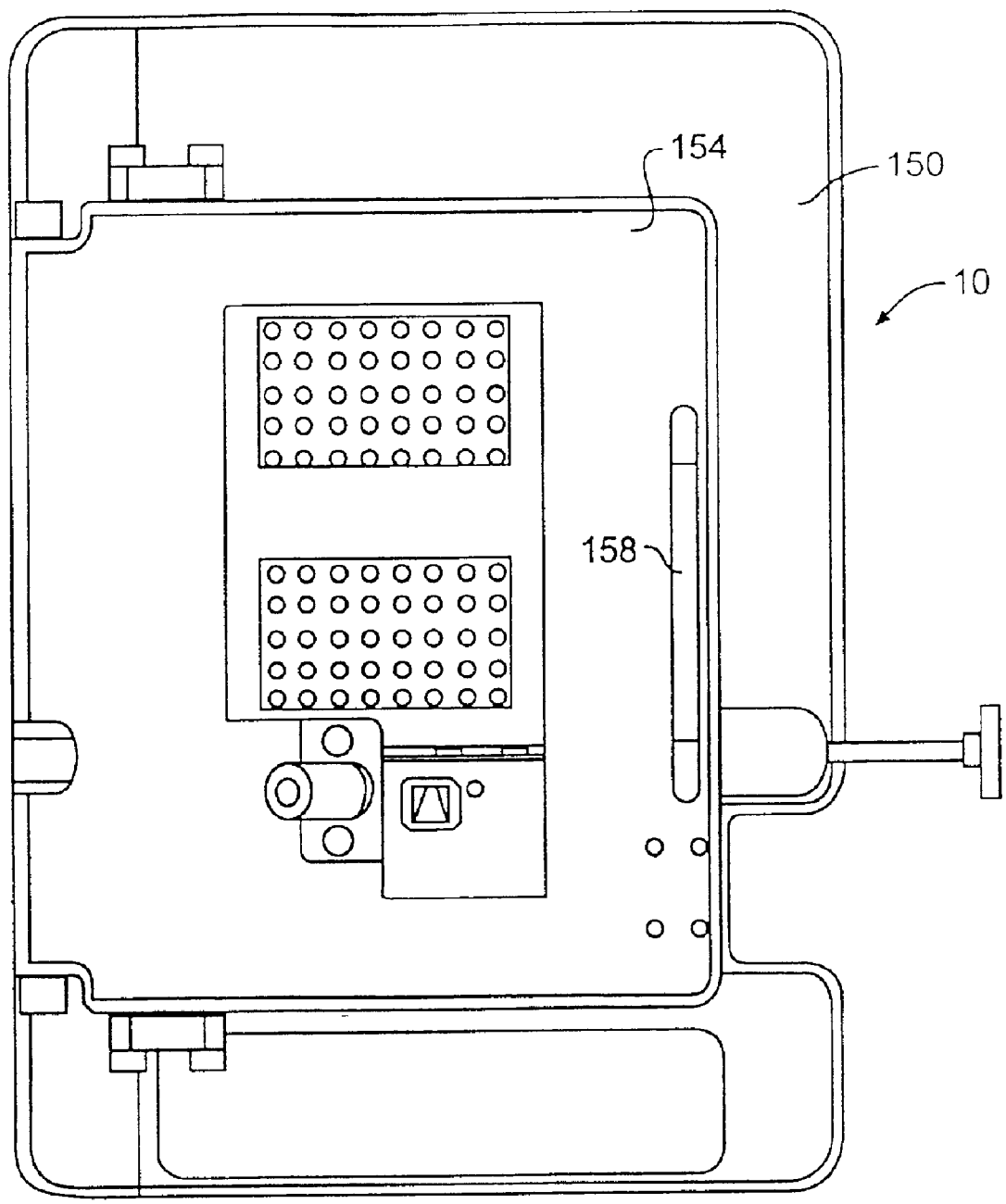
FIG. 15 shows a top view of the system of FIG. 1.
Figure 16:
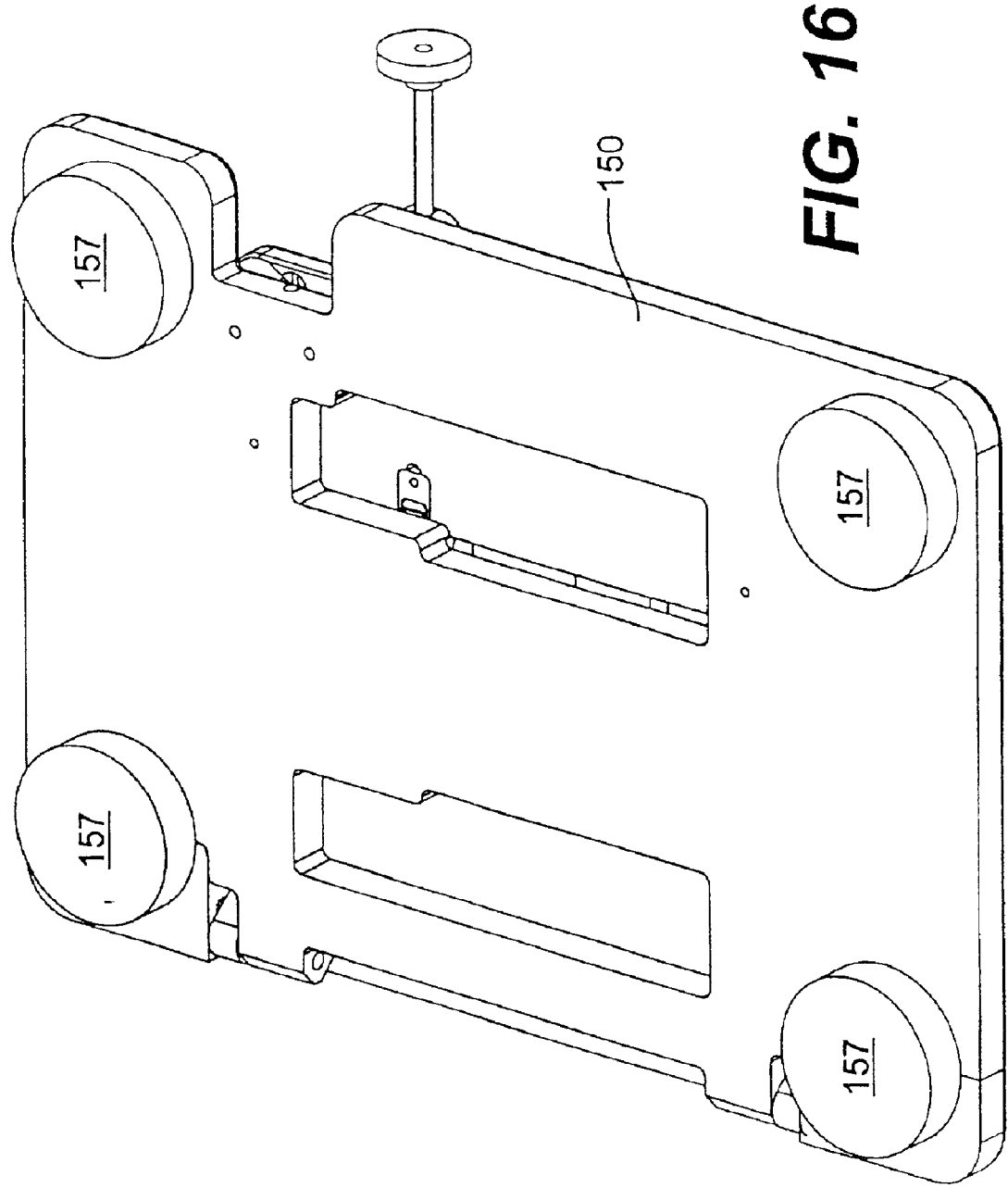
FIG. 16 shows a bottom perspective view of the filling station of FIG. 1.

The middle plate 152 further includes at least one through hole 184 for viewing the substrate. The middle plate further includes a vacuum hole 186 for closely mating with the vacuum port 72 on the adapter. The middle plate further includes a fill reservoir through hole 188 so that the fill reservoir 70 can project through the middle plate as shown in FIG. 14.

The middle plate 154 further includes a valving mechanism for opening and closing the fluid channels of the adapter. The valving mechanism includes an actuator knob 200 and actuator shaft 202 for reciprocating a set of wheels which can engage the top portion of the fluid channels to press and "pinch off" the channels. The actuator shaft 202 extends through an opening 204 in the middle plate to cause axial movement of the wheels. Other arrangements besides a knob and shaft may also be used. For example, the valving mechanism could include an automated mechanism such as pneumatic and/or solenoids for opening and closing the fluid channels of the adapter. Any suitable apparatus for opening and closing the fluid channels, either manually or automatically, may be utilized.

As embodied herein and shown in detail in FIGS. 18–24, the valving mechanism further includes a wheel assembly 206 for providing the engagement structures for opening and closing the fluid channels by reciprocation of the actuator knob. In the preferred embodiment, the wheel assembly 206 includes three wheels that can be identified as follows: vacuum wheel 210, fill wheel 212, and bladder wheel 214, as best shown in FIGS. 18–24. The vacuum wheel 210 and fill wheel 212 have identical widths, while the bladder wheel 214 has a larger width, as shown for example in FIG. 20. The bladder wheel 214 has this larger width in order to close off the wider main bladder channel 106, as shown in the drawings. The size and shape of the wheels can be varied. In addition, the wheels could be replaced by any other kind of engaging structures, for example, cam or other suitable surfaces. The main requirement is that the wheels or other valving surfaces be able to transmit sufficient force to close off fluid channels 86 in the adapter. The top and bottom plates of the adapter and the ridges 126 thereon are made out of flexible material so that the wheels or other valving surfaces can press down on the top plate 62 of the adapter and close off the corresponding fluid channels.

The wheels are mounted on a main wheel housing 216 as will be described. Each wheel is rotatably mounted in an individual wheel housing 218. A set screw 220 passes through a longitudinal opening 222 in the top of the main wheel housing 216. The end of each set screw 220 is threaded into a hole 224 on a flat surface 226 on the top of each individual wheel housing 218. At least one spring 228 is located between the head 230 of the set screw 220 and the top of the main wheel housing 216. In the preferred embodiment, spring 228 is a belleville washer, the threaded set screw 220 passing through the opening in the belleville washer. A second set of springs is located between a bottom surface of the main wheel housing 216 and the top surface 226 of the individual wheel housing 218. In the preferred embodiment, the second set of springs 240 are belleville washers. As shown in the drawings, in the preferred embodiment the set screw corresponding to the vacuum wheel 210 has two belleville washers 240 located below a bottom surface, and one belleville 228 washer located on top of the main wheel housing 216. The set screw corresponding to the fill wheel 212 and bladder wheel 214, respectively, has three belleville washers 240 located below a bottom surface and one belleville washer 228 located on top of the main wheel housing 216. The belleville washers allow for the wheels and set screws to have a slight amount of play relative to the main wheel housing. The wheels can move in a perpendicular direction to the adapter surface to adjust to the changes in surface on the top of the adapter. The provision of the springs allows the wheels to be adjusted to optimize performance of the filling station.

The valving mechanism further includes a return spring mechanism 242 for maintaining the actuator in a first position upon closing the filling station, and then returning the actuator to the first position, after the actuator knob 200 has been pulled to fill the substrate and the operator has opened the cover plate. As embodied herein and shown in FIGS. 23–24, return spring 244 is provided around a return spring shaft 246. The return spring 244 biases the actuator towards a first position. The first position, also referred to as the "actuator in" position, corresponds to the position where the actuator knob is pushed in or toward the middle plate. The second position, also referred to as the "actuator out" position, corresponds to the position where the actuator knob is pulled out away from the middle plate.

The filling station allows the liquid sample in the fill reservoir to be emptied into the substrate in a desirable manner. When the actuator is in the first position, the substrate can be evacuated due to the position of the wheels relative to the adapter. That is, in the first position with the actuator handle pushed in, the vacuum wheel 210 is located to the right of the vacuum channel 94 (as shown in FIG. 11). Accordingly, at the first position, the fill wheel 212 is located over and presses against the portion of the fill channel 100 between the juncture 96 to the exit port channel 98 and juncture 104 to the perpendicular portion of the fill channel 100. At this first position, the bladder wheel 214 is located over and presses against the main bladder channel 106 as shown in FIG. 11. It is preferable for the bladder wheel 214 to be positioned as close to the bladder connecting channel 105 as possible, while still remaining over the main bladder channel 106 as shown in FIG. 11. Accordingly, in the first position, there is free communication between the vacuum port 72, entrance 92 to the vacuum channel 94, the vacuum channel 94, the exit port channel 98 and the exit port 88. Therefore, a vacuum can be applied to the substrate by the vacuum source when the actuator is in this first position. In this first position, the sample fluid remains in the fill reservoir 70 because fluid flow is inhibited by the fill wheel 212 and bladder wheel 214.

When the actuator is moved to the second position, or "actuator out position," the vacuum channel 94 gets blocked by the vacuum wheel 210, thereby closing off the vacuum source. Any air trapped between the fill reservoir 70 and fill wheel 212 is pushed into bladder channel 106 and bladder connecting channel 105. This priming action presents this trapped air from entering the sample detection chamber in the substrate. The fill wheel 212 moves to the left in FIG. 11 (to the position labeled "2" in FIG. 11), so that the fill reservoir 70 can freely communicate with the exit port 88 of the adapter. Therefore, the liquid sample can flow from the fill reservoir 70 into the entrance 102 of the fill channel, through the fill channel 100, into exit port channel 98 and through the exit port 88 and exit port opening 90. Thereby, the network of passageways of the substrate can be filled when the actuator is in this second position.

In other words, the relative arrangement and spacings of the channels and the wheels (or other engaging surfaces) of the valving mechanism are such that the system is programmed to first apply a vacuum to evacuate the microcard, then to remove air from the system, then to open the fill reservoir to the evacuated microcard to permit the liquid sample to be loaded into the card.

The filling station shown in the figures is by way of example only. The filling station could consist of a variety of other designs. For example, instead of being pivotable relative to one another, the plates could be stacked one on top of the other and movable relative to one another to adjust the spacing thereof. In this alternate design, the plates would be spaced parallel from one another in order to insert the substrate and adapter into the filling station and then moved so that the plates are pressed against each other (and against the adapter and substrate) in a closed position. When in the closed position, an actuator similar to that described for the preferred embodiment may be used to open and close the fluid channels to fill the network of passageways of the substrate.

Additionally, the adapter and filling station may be modified to fill any type of suitable substrate or card. The present invention is not limited to the specific substrate shown in the drawings but could be usable with virtually any apparatus that can hold a liquid sample. For example, a tube could be connected to the exit port 88 to communication with a substrate.

The operation of the entire system will now be more completely described below. First, a substrate assembly, consisting of an substrate and an adapter, is provided. The substrate has a network of passageways including at least one sample detection chamber. The sample detection chambers 18 are each provided with analyte-specific reagents which are effective to react with a selected analyte which may be present in the liquid sample. These reagents typically include primers/probe sets that are provided in dry form in the sample detection chambers.

The reagents may be introduced into the sample detection chambers by any of a variety of methods. In one preferred method, prior to assembly of the top plate 32 and bottom plate 34 of the substrate, the primer/probe sets are dissolved into a solution. The top plates 32 are positioned upside down and an equal amount of the solution is then placed in each of the wells of the sample detection chambers 18 of the top plates by any known automatic or manual process. In a preferred method, a 96 well replicator is used to robotically deliver the solution to each of the sample detection chambers. The solution may also include certain chemicals, typically in the form of a gelatin so that the primer/probes will adhere to the wells. The upside down top plate 32 is then placed in a clean hood where the natural airflow evaporates the solution to "dry down" the reagent into the sample detection chambers. Exemplary types of reagents are described in full detail in WO97/36681 which is hereby incorporated by reference. If thermal cycling is later performed on the substrate, reaction between the reagents and the liquid sample from the fill reservoir may result in production of a detectable signal which indicates that the selected analyte is present.

The substrate assembly is placed inside the recess 155 of the base plate 150 of the filling station 16. The adapter 14 is aligned so that alignment pins 159 of the base plate project through the alignment holes 120 and 122 of the top and bottom plates. The attached substrate 12 is thus positioned so that the bottom surface of the bottom plate 34 of the substrate lays flat on the top surface of the recess 155. The filling station 16 is now closed by gripping the cover plate handle 158 and pivoting the cover plate 154 about hinge 156. The middle plate 152 pivots about the hinge 159 of the base plate, past the overcenter position so that the middle plate rests against the top surface of the base plate 150, while the cover plate 154 rests against the top surface of the middle plate 152. The overcenter linkage 180 ensures that the filling station will not be inadvertently opened.

In the closed position, the vacuum port 72 is sealingly placed inside vacuum hole 186 of the middle plate. The vacuum nipple 168 is also positioned inside the vacuum hole 186 so that the system can maintain a vacuum through the use of vacuum hose 166. The vacuum hose is connected to the vacuum nozzle 162 for connection to a vacuum pump (not shown).

In the closed position, the wheels of the wheel assembly 206 are pressed firmly against the adapter. The actuator should initially be maintained in a first position, or "actuator in" position. The return spring mechanism 242 ensures that the actuator will automatically assume this first position. At this first position, the vacuum wheel 210 is located to the right of the vacuum channel 94 (as seen in FIG. 11), while the fill wheel 212 blocks off the fill channel 100 to the right of the juncture 104. The fill wheel 212 obstructs the fill channel 100 by pressing against the top plate 62 and deforming the top plate so that it closes off the fill channel. Thus in the first position, there is free communication between the exit port 88 and the vacuum port 72.

A vacuum hose 166 is connected to the vacuum nozzle 162. The vacuum hose 166 is typically attached to a vacuum pump. The vacuum pump may be turned on before the vacuum hose 166 is attached to the vacuum nozzle 162 in order to begin evacuating the air in the vacuum hose. Upon connection of the hose to the nozzle, the air in the network of passageways of the substrate 12 and the vacuum channel 94 of the adapter 14 is evacuated. Preferably, a vacuum gauge (not shown) on the hose indicates the pressure inside the hose. When the vacuum gauge reaches a predetermined vacuum pressure, such as 50 microns, a liquid sample containing analytes can be introduced into the fill reservoir 72 which projects through the fill reservoir through hole 188 of the middle plate 152 as shown in FIG. 14. The liquid sample may be introduced into the fill reservoir by any conventional method, such as by the use of a hand held pipette. Other manual or automatic methods may also be used. The substrate 12 is now ready to be filled with the liquid sample.

The operator can fill the substrate by pulling on the actuator knob to move the actuator to a second or "actuator out" position. As the actuator knob 200 is pulled out, the wheels 210, 212, and 214 move along the main longitudinal channel of the adapter 14 to a second position. At the second position, the wheels allow the liquid sample in the fill reservoir 70 to flow into the substrate 12. The vacuum wheel 210 has moved to its second position between the exit port channel 98 and the vacuum channel 94, as best shown in FIG. 11. The vacuum wheel 210 thereby blocks off the communication between the vacuum port 72 and the exit port 88. The fill wheel 212 passes over the fill channel juncture 104, thereby exposing the fill reservoir to the vacuum in the substrate. Because there is lowered pressure in the network of passageways and exit port channel, the pressure differential with the atmosphere will urge the liquid sample through the fill channel 100, into the exit port channel 98 and into the network of passageways in the substrate. The liquid sample will then fill every empty space in the network of passageways, including the sample detection chambers 18. The process of filling the substrate can be accomplished in approximately 1–2 seconds in a typical operation, depending on a number of factors such as the level of vacuum, dimensions of the device and viscosity of sample solutions.

The filling process of the instant invention includes a "priming" arrangement that serves to minimize the presence of air entering the system. As the actuator is moved from the first position to the second position, the bladder wheel 214 and fill wheel 212 are moved to the left in FIG. 11. As the fill wheel 212 reaches the perpendicular portion of the fill channel 100, the bladder wheel 214 moves along the main bladder channel 106 the same distance as fill wheel 212. Because the bladder channel 106 is wider than the fill channel, the volume of air in the region between the bladder wheel and the fill wheel increases. This results in a decrease in the pressure of the air. The air below the fill reservoir 70 thus has a decreased pressure. The system is designed so that the pressure below the fill reservoir becomes less than the atmospheric pressure of the liquid sample. Consequently, a portion of the liquid sample flows into the fill channel 100 and the bladder connecting channel 105 removing air from the liquid sample in the process. Therefore, when the fill wheel 212 crosses over the perpendicular fill channel adjacent the juncture 104, there will be little or no air located in the fill channel 100 between the entrance 102 of the fill channel and the exit port 88. The fill reservoir 70 will now be exposed to the vacuum in the substrate, and consequently fill the network of passageways of the substrate.

After the substrate is filled, with the actuator still in the "out" position, the vacuum pump may be turned off. The filling station should now be opened immediately. During the step of opening the cover plate 154 and middle plate 152, the actuator will automatically return to the first position by the force of the return spring 244. The substrate assembly (adapter and substrate) can now be removed from the recess 155 in the base plate 150. The adapter 14 can then be peeled away from the substrate 12, along with the strip of adhesive (not shown) which was located between the adapter and substrate.

It is now desirable to seal the attachment/bladder groove 22 and sample inlet port 20 as soon as possible, in order to avoid contamination of the liquid sample in the network 17 of passageways and to prevent leakage of the liquid sample. In one embodiment shown in FIG. 25, a sealing tape 260 is provided in order to cover up and seal the attachment/bladder groove 22 and sample inlet port 20. The placement of the sealing tape 260 over the attachment/bladder groove 22 establishes the air pocket of the attachment/bladder groove as previously discussed.

In one embodiment, the sealing tape includes a plurality of holes 262. Each hole 262 is sized to be the same size as the raised portions 40 of the sample detection chambers 18, so that the sealing tape does not interfere with the sample detection chambers. In the illustrated embodiment, the sealing tape 260 includes eighteen holes, however any suitable number of holes may be provided. The sealing tape 260 has an adhesive on the bottom surface thereof so that it will sufficiently adhere to the top surface of the substrate.

Sealing tape 260 is made of any suitable material that is compatible with the intended use of the substrate. For example, for applications involving thermal cycling and/or PCR, the sealing tape should be capable of withstanding the changes in temperature and should not interfere with the PCR reaction. An example of an adhesive tape which is particularly suitable for a substrate to be used in PCR thermocycling is a 0.002" thick "DUPONT"™ "D" polyester laminated adhesive (3M Part No. 8142). Sealing tape 260 is also preferably clear so that the substrate can be more easily visually inspected.

The system and method according to the present invention reduces the amount of reagent that is used compared to larger sample well designs known in the art. The filling station arrangement allows the operator to fill the substrate with little contact with the microcard or fill reservoir. The procedure is fast and affordable. The procedure also allows for a slow priming of air out of the liquid to prevent air bubbles from occurring in the sample detection chambers. If air bubbles remain in the wells during PCR thermal cycling, they may expand and cause the reagents to exit the sample detection chambers. The system and method of the present invention substantially obviates many of these problems.

It will be apparent to those skilled in the art that various modifications and variations can be made in the apparatus and method for filling a substrate with a liquid sample, use of the apparatus of the present invention, and in construction of this apparatus, without departing from the scope or spirit of the invention. For instance, the system could be designed to fill multiple substrates at the same time. Various other types of liquid samples could be used besides the ones containing reagents.

In another aspect, the present invention includes apparatus and methods for focusing a plurality of light beams into a plurality of sample chambers, such as chambers 18 in substrate 12 discussed above. In one application, the apparatus may be employed to adapt the optics of a fluorescence detector so that the focus of each interrogating light beam is optimized for detecting a fluorescent signal in each of a plurality of sample chambers. According to one advantage of the invention, the apparatus is readily removable from a multi-sample fluorescence detection instrument, thereby enabling use of the instrument with a variety of multi-sample chamber configurations. Examples of suitable instruments for which the invention may be used include the PE Applied Biosystems 7700 Real Time PCR Instruments, and the apparatus set forth in U.S. Pat. No. 5,928,907, which is incorporated herein by reference. Reference will now be made to FIGS. 26A through 29D, which illustrate various features and components of an exemplary focusing apparatus in accordance with the invention.

Figure 26A:
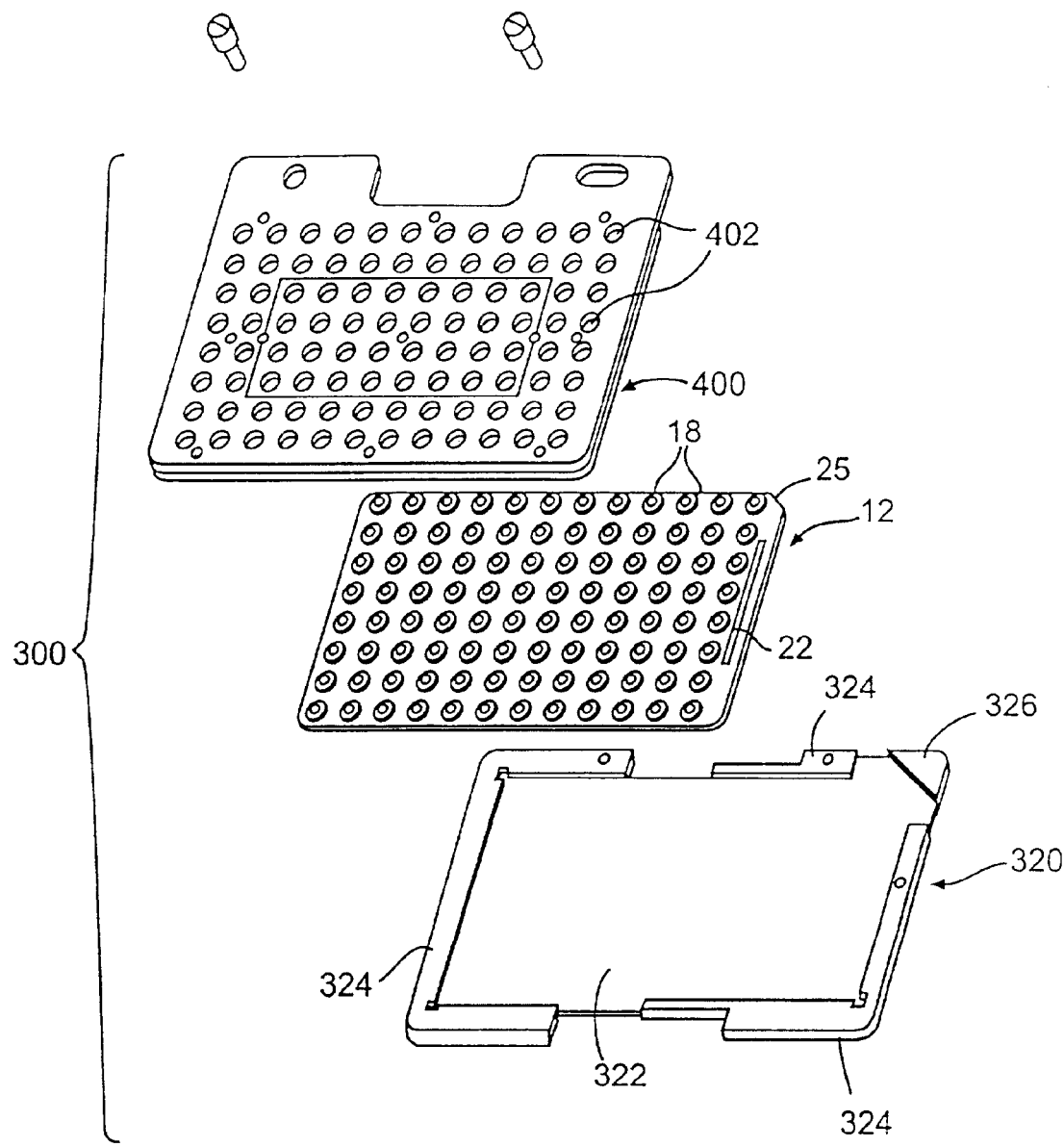
FIGS. 26A and 26B show an exploded perspective view (26A) and in-use view (26B), respectively, of an assembly including a support plate, multi-chamber substrate, and multi-lens focusing plate.

FIG. 26A shows an exploded perspective view of a focusing assembly 300 which comprises a support plate 320, a multi-chamber substrate 12 as discussed above, and a multi-lens focusing plate 400. Support plate 320 contains an upper surface 322 which is bordered by guide bars 324 that surround all or at least a selected portion of surface 322, for positioning a substrate 12 on the surface. Support plate 320 may additionally contain an angled guide bar 326 which is geometrically complementary to a beveled edge 25 of substrate 12, to ensure that the substrate has a consistent orientation relative to the support plate, and relative to the optical components of the instrument in which the assembly is to be placed for analysis. Typically, the guide bars are located on the support plate so as to provide a snug fit with the substrate. Although FIG. 26A shows guide bars 324 having a height that is approximately equal to the thickness of the substrate, the guide bars may have any other height that is compatible with use of the assembly. The support plate may be formed of any appropriate material having good thermal conductivity. Such material should also have low intrinsic fluorescence for the wavelength(s) being measured for signal measurement. Exemplary materials for forming the support plate include stainless steel, titanium, copper, silver, and aluminum.

Multi-lens focusing plate 400 generally contains a plurality of lenses 402 which are alignable with sample chambers 18 in substrate 12 and also with one or more detector elements in the detection instrument (not shown). Conveniently, lenses 402 are provided in an orthogonal X-Y array pattern which can be readily indexed for sample referencing and data collection, although any other suitable pattern can also be used.

The lenses may be held by or embedded in a plate comprising one or more layers. FIGS. 27 and 28A–28C illustrate an embodiment in which the focusing plate 400 comprises a lower sandwich plate 410, a lens-holding gasket 450, and an upper sandwich plate 470. Lower sandwich plate 410 includes a plurality of annular lens wells 412 each having a bottom rim 414 defined by (i) a counter-bore having a diameter approximately equal to the outer diameter of each lens 402 and extending from the upper surface 416 of plate 410 almost to lower surface 418 of plate 410, and (ii) a concentric through-hole of smaller diameter than the counter-bore which passes from the bottom of each lens well and through lower surface 418. The through-holes and counter-bores permit light to pass through the lower sandwich plate and into and out of the sample chambers, while providing rims 414 having annular dimensions sufficient to support the bottom of each lens.

In the exemplary configuration shown in the figures, each lens 402 has a flat lower surface which rests on a rim 414, a cylindrical side, and a convex upper surface having a radius selected to provide a desired change in the focus of light passing through the lens. For example, for use with a PE Applied Biosystems 7700 Real Time PCR Instrument, each lens can have a height of 2.5 mm (bottom to highest point of convex upper surface), a width of about 4.7 mm, and a convex surface curvature with a radius of about 4.7 mm. Such lenses are useful both for concentrating the light beams produced by the 7700 instrument and to shorten the focal length from about 0.5 inches below the plane of the substrate to zero, thereby significantly improving signal sensitivity. The lenses are preferably formed of a material having a minimal amount of intrinsic fluorescence, e.g., in the range of 500–700 nm for excitation by a 488 nm argon laser. An exemplary material is glass having an index of about 1.78 at 587.5 nm, and a surface quality of 80–50. Other materials such as polycarbonate are also suitable for the lenses. In addition, it will be appreciated that any other suitable lens configuration can be used to achieve the desired focusing.

Figure 28A:
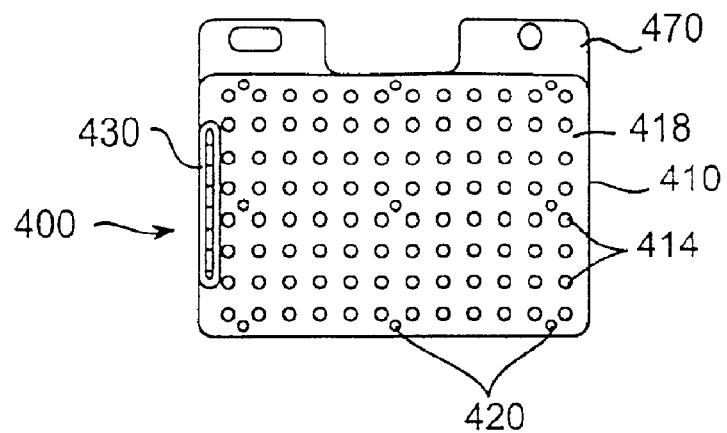
FIGS. 28A, 28B and 28C show, respectively, an overhead view (28A) and perspective view (28B) of the lower surface of the multi-lens focusing plate of FIGS. 26A and 26B, and a perspective view of the upper surface of the multi-lens focusing plate (28C)
Figure 28B:
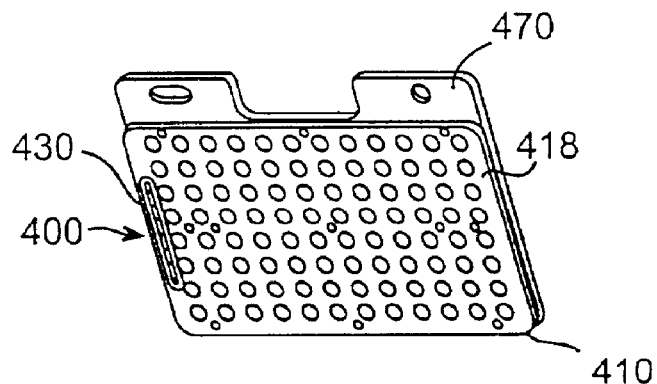
Figure 28C:
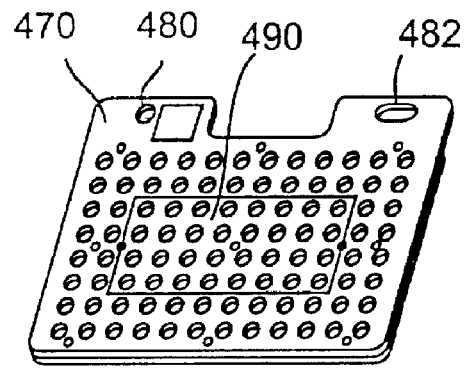
Figure 29A:
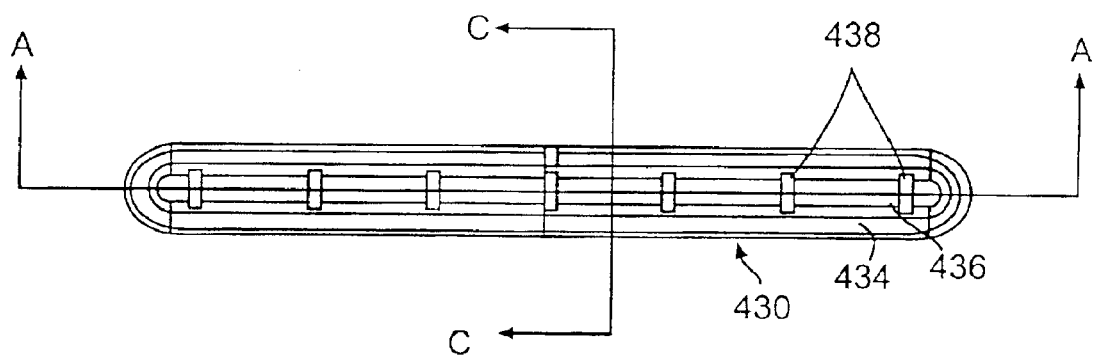
FIGS. 29A–29D show four views of a sealing gasket that can be included on the lower surface of the multi-lens focusing plate: an overhead view (29A), a cross-sectional view along line A—A (29B) of FIG. 29A, a cross-sectional view along line C—C (29C) of FIG. 29A, and a perspective view of the underside of the gasket (29D).
Figure 29B:
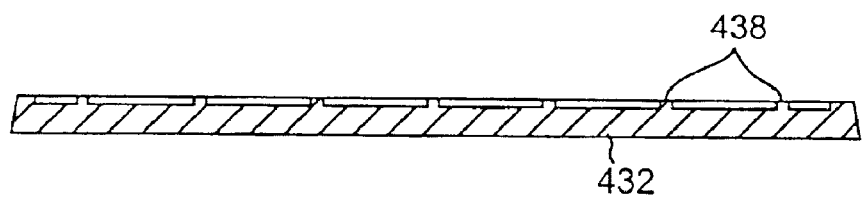
Figure 29C:
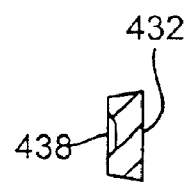
Figure 29D:
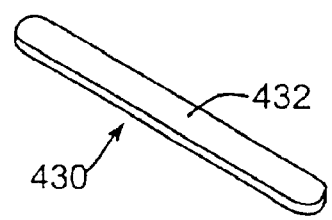

Lower surface 418 of lower sandwich plate 410 should be configured to provide uniform pressure across substrate 12. Also, to improve temperature control over the substrate, contacts between plate 410 and substrate 12 should be minimized to reduce thermal transfer therebetween. In FIGS. 28A and 28B, the diameters of the through-holes of wells 412 are selected to be smaller than the diameters of raised surfaces 40 on substrate 12, so that each through-hole rests tangentially on the domed portion of each raised surface 40, so that contact between plate 410 and substrate 12 is limited to a plurality of circular contacts near the top of each raised surface 40. This limited contact thus allows more careful control of heating and cooling from the bottom of support plate 320. Lower sandwich plate 410 may additionally include through-holes 420 for receiving pins or screws that join the lower sandwich plate 410 to gasket 450 and upper sandwich plate 470. Exemplary dimensions for plate 410 are as follows: 4.5 inch×3.0 inch (length×width), 0.12 inch (thickness), counter-bore diameter 0.19 inch, through-hole diameter 0.14 inch, and counter-bore depth 0.070 inch. These dimensions are by way of example only, as the plate may be made smaller or larger depending on the specific application. The plate can be made from any suitable material, such as polycarbonate, aluminum, etc.

With reference to FIGS. 28A and 28B, lower sandwich plate 410 may additionally include a sealing element 430 attached to lower surface 418, for covering and sealing attachment/bladder groove 22 of substrate 12 during temperature-cycling, if desired. Further details of an exemplary sealing element can be found in FIGS. 29A–29D. As shown in the figures, sealing element 430 has an elongate shape with a flat underside 432, an outer ridge 434 located along the entire circumference of the sealing element, and an interior cavity 436 within ridge 434. Cavity 436 additionally includes a plurality of ribs 438 to maintain rigidity and separation of opposing sides of outer ridge 434. When the lower surface of the lower sandwich plate is placed against the upper surface of substrate 12, sealing element 430 forms a tight seal over groove 22 and sealing tape 260 which covers groove 22 as discussed above. Sealing element 430 thus holds tape 260 tightly to the upper surface of the substrate 12 and further ensures that the liquid sample will not escape from groove 22 during temperature manipulations. Preferably, element 430 is formed by compression molding of a silicone material that is stable to high temperatures (e.g., 100° C.) and retains its shape at high pressure (e.g., 100 lbs), although any other suitable material can be used. The sealing element can have a variety of sizes and shapes, depending on a number of factors such as the size of the attachment/bladder groove 22 and the overall size of the substrate. For example, the sealing element can have dimensions of about 1.8 inch×0.20 inch.

Returning to FIG. 27, the multi-lens focusing plate 400 additionally includes a lens-holding gasket 450 which is useful for providing a plurality of arms above each lens to hold the lens 402 against the bottom of each lens well 412. Thus, gasket 450 contains an array of circular holes 452 having diameters slightly larger than the outer diameters of raised surfaces 40 of the substrate 12. Each hole 452 further includes four arms 454 located approximately 90 degrees from each other about the circumference of each hole and extending radially inward. Contact of gasket 450 with lower sandwich plate 410 causes the upper convex surfaces of the lenses to protrude slightly through the plane of holes 452, pushing the arms upward, thereby inducing slight pressure against the lenses and holding the lenses snugly in place. The gasket can be made of any suitable pliant material, such as dye-cut steel. Exemplary dimensions of gasket 450 are 112×76 mm (length×width), 0.13 mm thickness, hole diameter 6.4 mm, arm length 1.7 mm, arm width 1 mm. Gasket 450 may also include through-holes 456 to facilitate attachment of the gasket to the upper and lower sandwich plates.

Upper sandwich plate 470 comprises upper and lower surfaces 472 and 474, respectively, and an array of holes 476 which align with holes 452 and 412 in gasket 450 and lower sandwich plate 410, respectively. Plate 470 may additionally include an indentation bordered by tabs 478a and 478b to facilitate handling of the plate assembly. In the embodiment shown, tab 478a contains a circular positioning hole 480 for alignment with a corresponding peg located in the detection instrument (not shown), and an alignment slot 482 for alignment with a second peg in the detection instrument, to further constrain movement of the plate assembly. Upper surface 472 may additionally include a raised interior surface region 490. When substrate 12 is prepared to have a slightly bowed shape (middle of substrate is slightly elevated relative to a pair of opposing edges of the plate), region 490 is useful for transferring pressure from the top of multi-lens focusing plate 400 to the middle of substrate 12, thereby ensuring good contact along the entire lower surface of substrate 12 and the upper surface of support plate 320. This helps facilitate uniform temperature control via the support plate 320. Through-holes 484 can also be provided in upper sandwich plate 470 to allow plate 470, gasket 450, and plate 410 to be fastened together. Plate 470 is made of any suitable material, such as polycarbonate, aluminum, etc. Exemplary dimensions are 4.5×3.6 inches (length×width of plate), 2.83×1.42 inch (length×width of raised interior surface region 490), 0.105 inch (thickness of plate surrounding region 490), 0.015 inch (thickness of region 490), and 0.25 inch (radius of holes 476).

Figure 26B:
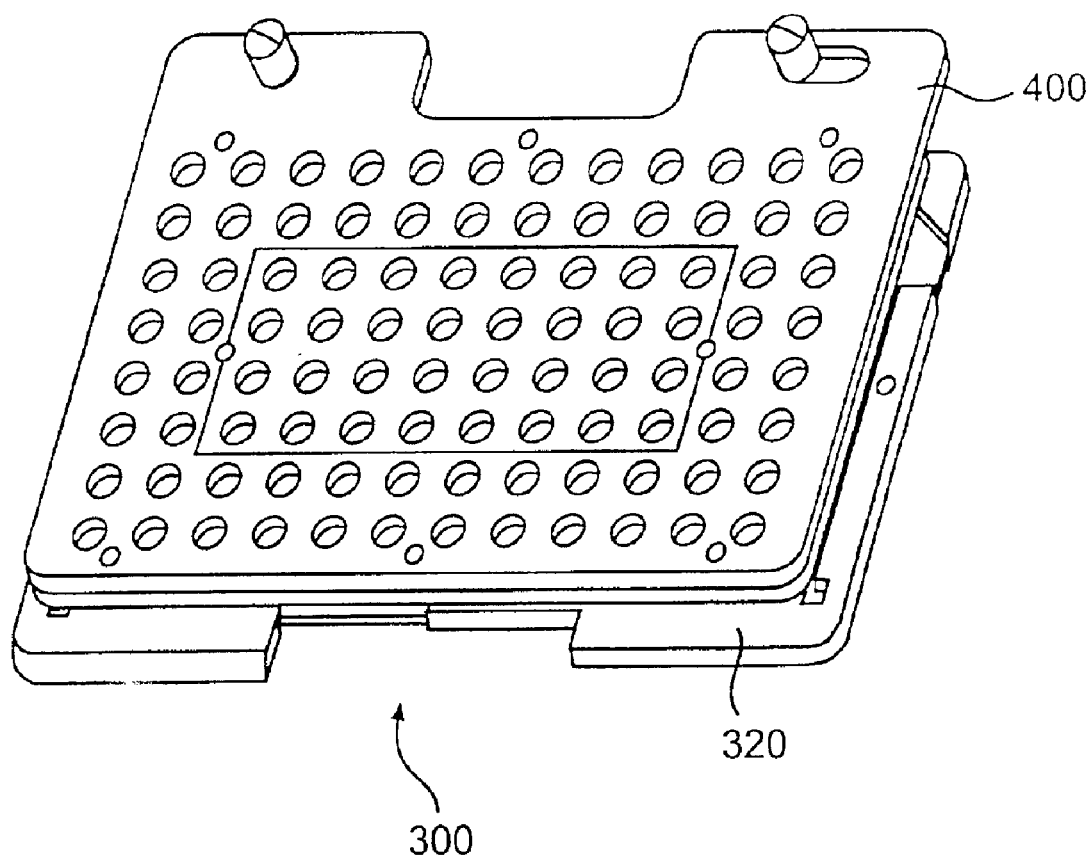
Figure 27:
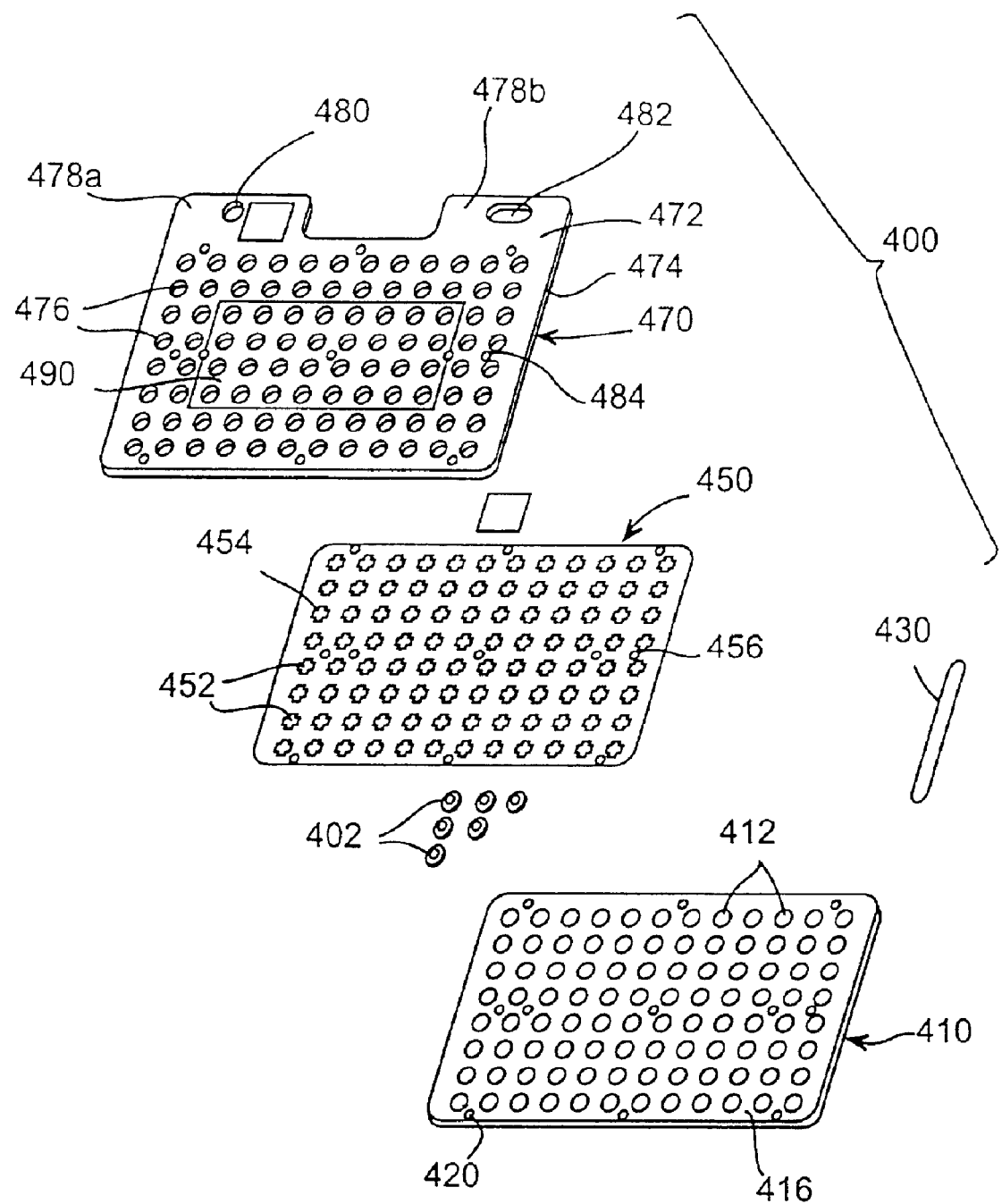
FIG. 27 shows an exploded perspective view of the multi-lens focusing plate of FIGS. 26A and 26B, which includes a lower sandwich plate, lens-holding gasket, and upper sandwich plate.

In practice, the plate assembly of FIGS. 26A and 26B can be utilized as follows. After the sample has been loaded into substrate 12, adapter 14 is removed, and groove 22 is covered with sealing tape 260 as discussed above. The sealed substrate is then placed on the flat surface of support 320 which may already have been placed in the detection instrument. Multi-lens focusing plate 400 is then placed over the substrate, with the circular positioning hole 480 aligning with a corresponding peg located in the detection instrument (not shown) and the alignment slot 482 aligning with a second peg in the detection instrument (not shown). The cover of the detection instrument, such as a PE Applied Biosystems 7700 Real Time PCR Instrument, is then contacted with the upper surface of plate 400 to press the entire assembly together. FIG. 26B shows the focusing assembly 300 in the resultant operative configuration. The instrument may then be programmed to subject the substrate to a selected number of cycles of heating and cooling, to accomplish target nucleic acid amplification or other processes, during which time, the sample chambers may be monitored to assess the course of amplification, for example. The time plots of signals measured over time can be used to ascertain the presence or absence of selected analytes. The substrate may then be discarded, but the other elements of the assembly can be reused if desired. Additional features of the invention are illustrated further by the following example.

EXAMPLE

The following "TAQMAN"™ PCR protocol was performed with a substrate 12 and assembly 300 substantially as described above. The principles of "TAQMAN"™ PCR are explained in the ABI Prism 7700 User's Manual, revision A, January 1998 available from PE Biosystems (Foster City, Calif., part #904989, incorporated herein by reference). A substrate was prepared containing probe sets effective to conduct amplification of two different target sequences in each sample detection chamber. In other words, each sample detection chamber contained a first probe set that was the same for all sample detection chambers, for amplifying a control target sequence, and a second probe set for amplifying a different target sequence in each chamber. Each probe set was selected to amplify a specific cDNA region having an average length of approximately 100 base pairs. The common probe set consisted of 0.2 femtomoles each of forward primer, reverse primer, and "TAQMAN"™ probe. Each different-sequence probe set consisted of 1.8 femtomoles of forward primer, 1.8 femtomoles of reverse primer, and 0.2 femtomoles of target-specific "TAQMAN"™ probe.

The sample loaded into substrate 12 was a mixture (150 $\mu$L) containing 200 nanograms of cDNA and 150 $\mu$L of "TAQMAN"™ Universal Master Mix (PE Biosystems, part #4304437). The cDNA was generated using a "TAQMAN"™ Gold RT-PCR kit (PE Biosystems, part #N808-0233), which contained the necessary reagents and protocol, the latter of which is incorporated herein by reference. The resulting 300 $\mu$L sample solution contained all the materials necessary for "TAQMAN"™ PCR except the primers and probe.

The sample solution was loaded into the substrate 12 using filling station 16 as described above. The substrate was placed into recess 155 of base plate 150 of the filling station, and the attached fill adapter 14 was aligned by placing the alignment holes 120 and 122 over the alignment pins 159 to the right of the recess. Cover plate 154 was closed so that the over-center hinge 180 snapped shut, pressing the middle plate 152 down on the substrate assembly. The vacuum pump was turned on. The vacuum was translated through a vacuum hose to the fill adapter/substrate assembly. After the pressure in the hose and network 17 of passageway fell below about 500 microns, as measured using an in-line vacuum gauge, sample solution (250 μL) was pipetted into fill reservoir 70. The actuator knob 200 was then pulled to the second position, allowing the sample to flow into the fluid channels and sample detection chambers 18 of the substrate. The vacuum pump was then turned off, and cover plate 154 was pulled open. Adapter 14 was removed from alignment pins 159 and the substrate/adapter assembly was removed from the fill station.

The adapter was removed from the substrate, along with the adhesive that had bound the two together, and adapter and adhesive were discarded. Sealing tape 260 was then placed over groove 22, sealing the liquid sample solution inside the substrate.

The card was then placed inside the ABI Prism 7700 Instrument using focusing assembly 300 as follows. First, the support plate 320 was placed on the thermal cycler block of the 7700 Instrument. Then the substrate 12 was loaded onto the support plate, followed by placement of the multi-lens focusing plate 400 on top of the substrate. The two alignment holes of the multi-lens assembly were placed over matching alignment pins of the 7700 Instrument. Finally, the cover of the 7700 Instrument was closed and tightened over assembly 300, which put pressure on the substrate and support plate.

The system was subjected to the following programmed thermal cycling protocol:

(1) 2 minutes at 50° C. and then 10 minutes at 99° C. to activate the enzymes in the sample solution.

(2) 35 cycles at 99° C. for 15 seconds and then 1 minute at 60° C. so that the cDNA in the sample solution would amplify exponentially.

The real-time data collected from the 7700 showed the expected amplifications for four unique target sequences, and no amplification for reaction chambers that contained probe sets for targets that were not expected to be in the sample. Also, the control assay that was common to each well showed an average detectable threshold of approximately 10 cycles. The four successful amplification reactions showed detectable thresholds of approximately 25–30 cycles.

It will be apparent to those skilled in the art that various modifications and variations can be made in the apparatus and method for positioning a substrate with a plurality of sample detection chambers in a detection unit, use of the apparatus of the present invention, and in construction of this apparatus, without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for positioning a plurality of sample detection chambers in a detection unit and a thermal cycling device, comprising:

a substrate positionable in a thermal cycling device having temperature control for heating and cooling the substrate, the substrate comprising a plurality of sample detection chambers, wherein the thermal cycling device is configured to subject the substrate to cycles of heating and cooling, and wherein the detection unit is configured to monitor nucleic acid amplification in the sample detection chambers; and a plate comprising:
a plurality of contacts with the substrate, wherein the plurality of contacts are positioned on a lower surface of the plate to provide uniform pressure across the substrate; and
a plurality of through holes, wherein the plurality of through holes permit light to pass to and from each sample detection chamber of the substrate to the detection unit and wherein the through holes are aligned between the sample detection chambers and the detection unit.

2. The apparatus of claim 1, wherein the plurality of contacts do not provide substantial thermal transfer between the substrate and the plate relative to the thermal transfer at a bottom surface of the substrate.

3. The apparatus of claim 1, wherein the substrate comprises a microcard.

* * * * *